(12) United States Patent
Rieunier et al.

(10) Patent No.: US 8,728,723 B2
(45) Date of Patent: May 20, 2014

(54) METHOD FOR SIMULTANEOUSLY DETECTING AN ANTIGEN OF, AND AN ANTIBODY AGAINST, AN INFECTIOUS MICROORGANISM

(75) Inventors: François Rieunier, Bois d'Arcy (FR); Muriel Feyssaguet, Saint Cloud (FR); Stéphanie Henriot, Suresnes (FR); Nadine Lambert, Chatou (FR)

(73) Assignee: Bio-Rad Innovations, Marnes la Coquette (FR)

( * ) Notice: Subject to any disclaimer, the term of this patent is extended or adjusted under 35 U.S.C. 154(b) by 0 days.

(21) Appl. No.: 13/435,325

(22) Filed: Mar. 30, 2012

(65) Prior Publication Data

US 2013/0157255 A1 Jun. 20, 2013

Related U.S. Application Data

(62) Division of application No. 12/076,090, filed on Mar. 13, 2008, now Pat. No. 8,168,394, which is a division of application No. 10/431,587, filed on May 8, 2003, now Pat. No. 7,364,860.

(60) Provisional application No. 60/379,146, filed on May 10, 2002.

(51) Int. Cl.
*C12Q 1/70* (2006.01)
*C12N 7/00* (2006.01)

(52) U.S. Cl.
USPC ............................................ 435/5; 424/208.1

(58) Field of Classification Search
None
See application file for complete search history.

(56) References Cited

U.S. PATENT DOCUMENTS

| 4,870,003 | A | 9/1989 | Kortright et al. |
| 5,627,026 | A | 5/1997 | O'Connor et al. |
| 6,383,740 | B2 | 5/2002 | Collins |
| 6,432,633 | B1 | 8/2002 | Yamamoto et al. |
| 6,593,079 | B1 * | 7/2003 | Donie et al. ...................... 435/5 |
| 6,623,921 | B2 | 9/2003 | Aoyagi et al. |
| 6,762,032 | B1 * | 7/2004 | Nelson et al. ................. 435/7.21 |
| 6,855,809 | B2 * | 2/2005 | Shah et al. ..................... 530/350 |

FOREIGN PATENT DOCUMENTS

| EP | 0173295 | 5/1986 |
| EP | 0363025 | 4/1990 |
| EP | 0388232 | 9/1990 |
| EP | 0442394 | 8/1991 |
| EP | 0451891 | 10/1991 |
| GB | 2313666 | 12/1997 |
| WO | WO 92/22571 | 12/1992 |
| WO | WO 93/03376 | 2/1993 |
| WO | WO 93/21346 | 10/1993 |
| WO | WO 95/23973 | 9/1995 |
| WO | WO 95/32206 | 12/1995 |
| WO | WO 98/40744 | 9/1998 |
| WO | WO 99/45395 | 9/1999 |
| WO | WO 01/04149 | 1/2001 |
| WO | WO 01/096875 | 12/2001 |

OTHER PUBLICATIONS

Kuo et al "An assay for circulating antibodies to a major eliologic virus . . ." Science 244(4902):362-364 (Apr. 21, 1989).
Stuyver et al. Abstract fo database accession No. q68685; XP002237193 (1995) one page.
Kalinina et al. A natural intergenotypic recombinant of hepatitis C virus identified in St. Petersburg,: Journal of Virology 76(8):4034-4043 (Apr. 2002).

* cited by examiner

*Primary Examiner* — Agnieszka Boesen
(74) *Attorney, Agent, or Firm* — Jacobson Holman PLLC

(57) ABSTRACT

The invention relates to a method for detecting, in vitro, an infection with a microorganism, such as the hepatitis C virus, in a biological sample, by simultaneously detecting an antigen of this microorganism and the antibodies against this same antigen, and also to the reagents and kits implementing this method.

9 Claims, 1 Drawing Sheet

Figure 1:
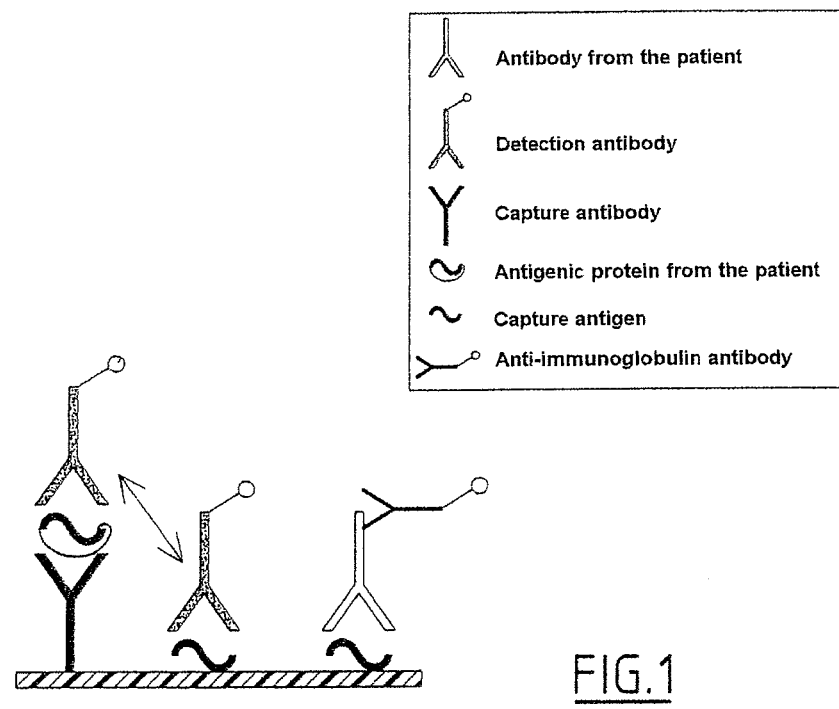

SEQUENCE LISTING

<160> NUMBER OF SEQ ID NOS: 33

<210> SEQ ID NO 1
<211> LENGTH: 75
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

```
Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Ser
 65                  70                  75

<210> SEQ ID NO 2
<211> LENGTH: 63
<212> TYPE: PRT
<213> ORGANISM: Hepatitis C virus

<400> SEQUENCE: 2

Lys Pro Gln Arg Lys Thr Lys Arg Asn Thr Asn Arg Arg Pro Gln Asp
 1               5                  10                  15

Val Lys Phe Pro Gly Gly Gly Gln Ile Val Gly Gly Val Tyr Leu Leu
             20                  25                  30

Pro Arg Arg Gly Pro Arg Leu Gly Val Arg Ala Thr Arg Lys Thr Ser
         35                  40                  45

Glu Arg Ser Gln Pro Arg Gly Arg Arg Gln Pro Ile Pro Lys Ala
 50                  55                  60

<210> SEQ ID NO 3
<211> LENGTH: 53
<212> TYPE: PRT
<213> ORGANISM: Hepatitis C virus

<400> SEQUENCE: 3

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser
     50

<210> SEQ ID NO 4
<211> LENGTH: 75
<212> TYPE: PRT
<213> ORGANISM: Hepatitis C virus

<400> SEQUENCE: 4

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Gly Tyr Leu Leu Pro Arg Arg Gly Pro Arg Gly Gly Val Gly Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Ser
 65                  70                  75

<210> SEQ ID NO 5
<211> LENGTH: 75
<212> TYPE: PRT
<213> ORGANISM: Hepatitis C virus
```

```
<400> SEQUENCE: 5

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Gly Gly
            20                  25                  30

Gly Val Tyr Leu Leu Pro Arg Arg Gly Pro Arg Gly Val Gly Ala
            35                  40                  45

Thr Arg Lys Thr Ser Glu Arg Ser Gln Pro Arg Gly Arg Gln Pro
        50                  55                  60

Ile Pro Lys Ala Arg Arg Pro Glu Gly Arg Ser
65                  70                  75

<210> SEQ ID NO 6
<211> LENGTH: 75
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Gly Leu Pro Arg Arg Gly Pro Arg Gly Val Gly Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser
65                  70                  75

<210> SEQ ID NO 7
<211> LENGTH: 63
<212> TYPE: PRT
<213> ORGANISM: Hepatitis C virus

<400> SEQUENCE: 7

Lys Pro Gln Arg Lys Thr Lys Arg Asn Thr Asn Arg Arg Pro Gln Asp
1               5                   10                  15

Val Lys Phe Pro Gly Gly Gly Gln Ile Val Gly Gly Gly Tyr Leu Leu
            20                  25                  30

Pro Arg Arg Gly Pro Arg Gly Val Gly Ala Thr Arg Lys Thr Ser
            35                  40                  45

Glu Arg Ser Gln Pro Arg Gly Arg Arg Gln Pro Ile Pro Lys Ala
        50                  55                  60

<210> SEQ ID NO 8
<211> LENGTH: 63
<212> TYPE: PRT
<213> ORGANISM: Hepatitis C virus

<400> SEQUENCE: 8

Lys Pro Gln Arg Lys Thr Lys Arg Asn Thr Asn Arg Arg Pro Gln Asp
1               5                   10                  15

Val Lys Phe Pro Gly Gly Gly Gln Ile Gly Gly Gly Val Tyr Leu Leu
            20                  25                  30

Pro Arg Arg Gly Pro Arg Gly Val Gly Ala Thr Arg Lys Thr Ser
            35                  40                  45

Glu Arg Ser Gln Pro Arg Gly Arg Arg Gln Pro Ile Pro Lys Ala
        50                  55                  60
```

```
<210> SEQ ID NO 9
<211> LENGTH: 70
<212> TYPE: PRT
<213> ORGANISM: Hepatitis C virus

<400> SEQUENCE: 9

Lys Pro Gln Arg Lys Thr Lys Arg Asn Thr Asn Arg Arg Pro Gln Asp
1               5                   10                  15

Val Lys Phe Pro Gly Gly Gly Gln Ile Val Gly Gly Val Tyr Gly Leu
            20                  25                  30

Pro Arg Arg Gly Pro Arg Gly Gly Val Gly Ala Thr Arg Lys Thr Ser
        35                  40                  45

Glu Arg Ser Gln Pro Gly Arg Arg Gln Pro Ile Pro Lys Ala Arg
    50                  55                  60

Arg Pro Glu Gly Arg Ser
65                  70

<210> SEQ ID NO 10
<211> LENGTH: 53
<212> TYPE: PRT
<213> ORGANISM: Hepatitis C virus

<400> SEQUENCE: 10

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Gly Tyr Leu Leu Pro Arg Arg Gly Pro Arg Gly Gly Val Gly Ala
        35                  40                  45

Thr Arg Lys Thr Ser
    50

<210> SEQ ID NO 11
<211> LENGTH: 53
<212> TYPE: PRT
<213> ORGANISM: Hepatitis C virus

<400> SEQUENCE: 11

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Gly Gly
            20                  25                  30

Gly Val Tyr Leu Leu Pro Arg Arg Gly Pro Arg Gly Gly Val Gly Ala
        35                  40                  45

Thr Arg Lys Thr Ser
    50

<210> SEQ ID NO 12
<211> LENGTH: 53
<212> TYPE: PRT
<213> ORGANISM: Hepatitis C virus

<400> SEQUENCE: 12

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

Gly Val Tyr Gly Leu Pro Arg Arg Gly Pro Arg Gly Gly Val Gly Ala
            35                  40                  45

Thr Arg Lys Thr Ser
    50

<210> SEQ ID NO 13
<211> LENGTH: 73
<212> TYPE: PRT
<213> ORGANISM: Hepatitis C virus

<400> SEQUENCE: 13

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Gly Tyr Leu Leu Pro Arg Arg Gly Pro Arg Leu Arg Ala Thr Arg
        35                  40                  45

Lys Thr Ser Glu Arg Ser Gln Pro Arg Gly Arg Gln Pro Ile Pro
    50                  55                  60

Lys Ala Arg Arg Pro Glu Gly Arg Ser
65                  70

<210> SEQ ID NO 14
<211> LENGTH: 75
<212> TYPE: PRT
<213> ORGANISM: Hepatitis C virus
<220> FEATURE:
<221> NAME/KEY: MOD_RES
<222> LOCATION: (45)..(45)
<223> OTHER INFORMATION: bAla

<400> SEQUENCE: 14

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Gly Tyr Leu Leu Pro Arg Arg Gly Pro Arg Leu Ala Val Arg Ala
        35                  40                  45

Thr Arg Lys Thr Ser Glu Arg Ser Gln Pro Arg Gly Arg Gln Pro
    50                  55                  60

Ile Pro Lys Ala Arg Arg Pro Glu Gly Arg Ser
65                  70                  75

<210> SEQ ID NO 15
<211> LENGTH: 76
<212> TYPE: PRT
<213> ORGANISM: Hepatitis C virus

<400> SEQUENCE: 15

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Gly Tyr Leu Leu Pro Arg Arg Gly Pro Arg Leu Gly Gly Arg
        35                  40                  45

Ala Thr Arg Lys Thr Ser Glu Arg Ser Gln Pro Arg Gly Arg Gln
    50                  55                  60

Pro Ile Pro Lys Ala Arg Arg Pro Glu Gly Arg Ser
65                  70                  75

<210> SEQ ID NO 16
<211> LENGTH: 75
<212> TYPE: PRT
<213> ORGANISM: Hepatitis C virus
<220> FEATURE:
<221> NAME/KEY: MOD_RES
<222> LOCATION: (29)..(29)
<223> OTHER INFORMATION: Nle

<400> SEQUENCE: 16

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Leu Gly Val Gly
                20                  25                  30

Gly Val Tyr Leu Leu Pro Arg Arg Gly Pro Arg Gly Gly Val Gly Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser
65                  70                  75

<210> SEQ ID NO 17
<211> LENGTH: 75
<212> TYPE: PRT
<213> ORGANISM: Hepatitis C virus

<400> SEQUENCE: 17

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Gly Phe Leu Leu Pro Arg Arg Gly Pro Arg Gly Gly Val Gly Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser
65                  70                  75

<210> SEQ ID NO 18
<211> LENGTH: 75
<212> TYPE: PRT
<213> ORGANISM: Hepatitis C virus
<220> FEATURE:
<221> NAME/KEY: MISC_FEATURE
<222> LOCATION: (35)..(35)
<223> OTHER INFORMATION: homo-serine

<400> SEQUENCE: 18

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Gly Ser Leu Leu Pro Arg Arg Gly Pro Arg Gly Gly Val Gly Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser
65                  70                  75

```
<210> SEQ ID NO 19
<211> LENGTH: 4
<212> TYPE: PRT
<213> ORGANISM: Hepatitis C virus

<400> SEQUENCE: 19

Leu Gly Val Arg
1

<210> SEQ ID NO 20
<211> LENGTH: 7
<212> TYPE: PRT
<213> ORGANISM: Hepatitis C virus

<400> SEQUENCE: 20

Ile Val Gly Gly Val Tyr Leu
1               5

<210> SEQ ID NO 21
<211> LENGTH: 6
<212> TYPE: PRT
<213> ORGANISM: Hepatitis C virus

<400> SEQUENCE: 21

Gln Ile Val Gly Gly Val
1               5

<210> SEQ ID NO 22
<211> LENGTH: 58
<212> TYPE: PRT
<213> ORGANISM: Human immunodeficiency virus type 1

<400> SEQUENCE: 22

Phe Arg Gly Tyr Val Gly Arg Phe Tyr Lys Thr Leu Arg Ala Glu Gln
1               5                   10                  15

Ala Gly Gln Gly Val Lys Asn Phe Met Thr Glu Thr Leu Leu Val Gln
            20                  25                  30

Asn Ala Asn Pro Asp Cys Lys Thr Ile Leu Lys Ala Leu Gly Pro Ala
        35                  40                  45

Ala Thr Leu Glu Glu Met Met Thr Ala Cys
    50                  55

<210> SEQ ID NO 23
<211> LENGTH: 58
<212> TYPE: PRT
<213> ORGANISM: Human immunodeficiency virus type 1

<400> SEQUENCE: 23

Phe Arg Asp Tyr Val Asp Arg Phe Tyr Lys Thr Leu Arg Ala Glu Gln
1               5                   10                  15

Ala Ser Gln Glu Val Lys Asn Trp Met Thr Glu Thr Leu Leu Val Gln
            20                  25                  30

Asn Ala Asn Pro Asp Cys Lys Thr Ile Leu Lys Ala Leu Gly Pro Ala
        35                  40                  45

Ala Thr Leu Glu Glu Met Met Thr Ala Cys
    50                  55

<210> SEQ ID NO 24
<211> LENGTH: 15
<212> TYPE: PRT
<213> ORGANISM: Human immunodeficiency virus type 1
```

-continued

```
<400> SEQUENCE: 24

Gln Ala Ser Gln Glu Val Lys Asn Trp Met Thr Glu Thr Leu Leu
1               5                   10                  15

<210> SEQ ID NO 25
<211> LENGTH: 15
<212> TYPE: PRT
<213> ORGANISM: Human immunodeficiency virus type 2

<400> SEQUENCE: 25

Gln Thr Asp Pro Ala Val Lys Asn Trp Met Thr Gln Thr Leu Leu
1               5                   10                  15

<210> SEQ ID NO 26
<211> LENGTH: 12
<212> TYPE: PRT
<213> ORGANISM: Human immunodeficiency virus type 1

<400> SEQUENCE: 26

Leu Gly Leu Trp Gly Cys Ser Gly Lys Leu Ile Cys
1               5                   10

<210> SEQ ID NO 27
<211> LENGTH: 12
<212> TYPE: PRT
<213> ORGANISM: Human immunodeficiency virus type 1

<400> SEQUENCE: 27

Leu Gly Ile Trp Gly Cys Ser Gly Lys Leu Ile Cys
1               5                   10

<210> SEQ ID NO 28
<211> LENGTH: 12
<212> TYPE: PRT
<213> ORGANISM: Human immunodeficiency virus type 1

<400> SEQUENCE: 28

Leu Gly Leu Trp Gly Cys Ser Gly Lys His Ile Cys
1               5                   10

<210> SEQ ID NO 29
<211> LENGTH: 12
<212> TYPE: PRT
<213> ORGANISM: Human immunodeficiency virus type 1

<400> SEQUENCE: 29

Leu Gly Met Trp Gly Cys Ser Gly Lys His Ile Cys
1               5                   10

<210> SEQ ID NO 30
<211> LENGTH: 26
<212> TYPE: PRT
<213> ORGANISM: Human immunodeficiency virus type 1

<400> SEQUENCE: 30

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys
            20                  25

<210> SEQ ID NO 31
<211> LENGTH: 34
<212> TYPE: PRT
<213> ORGANISM: Human immunodeficiency virus type 1
```

```
<400> SEQUENCE: 31

Arg Ile Leu Ala Val Glu Arg Tyr Leu Lys Asp Gln Gln Leu Leu Gly
1               5                   10                  15

Ile Trp Gly Ser Gly Lys Leu Ile Cys Thr Thr Ala Val Pro Trp Asn
            20                  25                  30

Ala Ser

<210> SEQ ID NO 32
<211> LENGTH: 12
<212> TYPE: PRT
<213> ORGANISM: Human immunodeficiency virus type 2

<400> SEQUENCE: 32

Leu Asn Ser Trp Gly Cys Ala Phe Arg Gln Val Cys
1               5                   10

<210> SEQ ID NO 33
<211> LENGTH: 36
<212> TYPE: PRT
<213> ORGANISM: Human immunodeficiency virus type 2

<400> SEQUENCE: 33

Arg Val Thr Ala Ile Glu Lys Tyr Leu Gln Asp Gln Ala Arg Leu Asn
1               5                   10                  15

Ser Trp Gly Cys Ala Phe Arg Gln Val Cys His Thr Thr Val Pro Trp
            20                  25                  30

Val Asn Asp Ser
            35
```

METHOD FOR SIMULTANEOUSLY DETECTING AN ANTIGEN OF, AND AN ANTIBODY AGAINST, AN INFECTIOUS MICROORGANISM

This is a divisional of Ser. No. 12/076,090 filed Mar. 13, 2008, now U.S. Pat. No. 8,168,394 which is a divisional of Ser. No. 10/431,587 filed May 8, 2003, now U.S. Pat. No. 7,364,860 which claims the benefit of U.S. Provisional Application No. 60/379,146, filed May 10, 2002.

The invention relates to the in vitro detection of an infection with an infectious, in particular viral, microorganism, and in particular the in vitro detection of an infection with a hepatitis C virus (HCV). More precisely, the invention also relates to a method for simultaneously detecting an antigen of an infectious, in particular viral, microorganism, and antibodies directed against this same infectious microorganism, and also to the reagents and kits implementing it. More particularly, it relates to a method for simultaneously detecting HCV antigen and anti-HCV antibodies, and to the reagents and kits implementing it.

Infection with the hepatitis C virus, a form of hepatitis initially referred to as hepatitis non-A, non-B, is a preoccupying health problem which has been recognized for a long time, in particular in blood transfusion.

Patent application EP 318 216 published on May 31, 1989, describes the cloning of fragments of cDNA of a virus responsible for hepatitis C in humans, called HCV. It also describes the sequence of five genes encoding the nonstructural proteins (NS1 to NS5) of the virus (approximately 78% of the total genome of HCV), the C100-3 antigen (which contains 363 amino acids of the NS3-NS4 region and is fused to superoxide dismutase) and also a method for detecting anti-HCV antibodies using the C100-3 antigen. This "first generation" method for detecting anti-HCV antibodies made it possible, inter glia, to establish that HCV is a major cause of hepatitis non-A, non-B, now called hepatitis C in the world. However, this method does not make it possible to detect more than 70 to 80% of the sera infected with the virus. This lack of sensitivity does not allow early detection of the infections either.

Okamoto et al. (1990a) and patent application EP 388 232 published on Sep. 19, 1990, describe the 5' terminal sequence of the genome of the HCV virus, that is to say the sequence of genes encoding the structural proteins (capsid, matrix, envelope) of the virus responsible for hepatitis C.

Okamoto et al. (1990b) have published the use of the sequence of amino acids 39-74 of the HCV capsid as a target for detection by ELISA of anti-HCV antibodies.

The article Hosein et al. (1991) describes an immunoassay for detecting anti-HCV antibodies based on the use of structural (capsid: in the region AA 1-120) and nonstructural (NS3-NS4: in the region AA 1200-1800) synthetic peptide antigens. It demonstrates the advantage of the synthetic peptides in the detection of anti-HCV antibodies, and of the combination of the structural and nonstructural antigens: the combination increases the sensitivity and therefore the earliness of detection. The assay described here makes it possible to detect antibodies 4 to 10 weeks earlier. The article also shows that there is no major immunodominant epitope, as is known to be the case, for example, in AIDS viruses.

Nasoff et al. (1991) note that most of the dominant immunoreactive epitopes of the capsid are located in the N-terminal region (AA 1-40) and that antibodies directed against these epitopes appear soon after infection.

The "second generation" assays for detecting anti-HCV antibodies (that is to say assays based on the simultaneous use of nonstructural and structural capture antigens) constitute a significant progress with respect to the first generation assays. However, they still lack sensitivity: specifically, they detect at best 95 to 98% of the sera taken from patients contaminated with HCV. Consequently, this detection is still not early enough and still allows infected blood donations to get through unnoticed in blood transfusion. In fact, in order to reduce the post-transfusion risks, it is necessary to detect the presence of the virus itself, before the appearance of antibodies, and as early as possible after contamination. This period between contamination and seroconversion (i.e. the appearance of antibodies) is referred to as the "serological window".

Various teams (Garson et al. (1990); Shieh et al. (1991)) have proposed the detection of the viral RNA by PCR (polymerase chain reaction) in order to solve the problem of sensitivity and of earliness mentioned above. This method in fact allows extremely sensitive and early detection of the infection with HCV, that is to say only a few days after exposure to the virus, namely 4 to 8 weeks before the increase in circulating antiviral antibodies. It currently constitutes the method of reference for detecting the virus in biological fluids.

However, the PCR method applied to HCV comes up against various difficulties. Firstly, it involves carrying out pre-steps of extraction, purification of RNA, and then reverse transcription of the RNA to cDNA, and part of the viral material is lost in the course of these prior steps. Secondly, it requires specific and expensive amplification equipment. In addition, it does not make it possible to simultaneously process a large number of samples and often gives rise to contamination.

Another approach, aimed at early detection of the infection with HCV, has consisted in detecting the circulating viral antigen (capsid). This antigen also appears several weeks before the appearance of the serum anti-HCV antibodies. Takahashi et al. (1992) describe an ELISA technique which detects the capsid antigen using a pair of antibodies.

However, the detection of this antigen is difficult to set up due in large part to the low titer of detectable antigen in the blood and to the quality of the available immunoreagents.

Hajime Tokita et al. (2000) describe a sandwich-type immunoassay using a pair of monoclonal antibodies (5F11 and 5E3), known on the market as "Immucheck F HCV Ag Core Kokusai", which gives very sensitive detection. The authors of this article emphasize that a mutation, Thr49Pro, in the capsid protein reduces the sensitivity of the assay. Also seeking to detect the capsid antigen at an early stage, Peterson et al. (2000) sets out an ELISA technique for detecting the capsid antigen of HCV using anti-capsid monoclonal antibodies without pretreatment of the sample. The article shows, by virtue of comparing three independent assays (detection of the HCV RNA by PCR, and of the anti-HCV antibodies and of the capsid antigen by ELISA), that, thus, the circulating HCV capsid antigen can be usefully detected in blood bags taken during the early seronegative phase of the infection (namely approximately 1 day after detection of the RNA).

Earliness of detection of infection with the hepatitis C virus, combined with the possibility of detecting the antibody responses subsequent to seroconversion throughout the duration of the infection, remains a current aim, most particularly in transfusion.

From the viewpoint of having a simple, sensitive, specific, reproducible, inexpensive method which is easy to implement and can be automated—with a view to mass screening—for detecting, firstly, the HCV antigen during the period of the serological window, and then following the serological evolution of the patient after seroconversion, combining detection of the anti-HCV antibodies and detection of an HCV antigen is most desirable.

However, this poses a major problem; that of the interference, with respect to the assaying of the HCV antigen, between the anti-HCV antibodies present in the serum and labeled anti-HCV antibodies. Thus, the introduction onto a solid phase, for the purpose of detecting a given antibody, of a target antigen which would have the same epitopes as those recognized by the labeled antibody or antibodies used for the purpose of the simultaneous sandwich detection of an antigen, would irreparably lead to attachment of labeled antibody or antibodies to the solid phase and therefore to the assay giving a falsely positive response.

This is particularly true in a system for simultaneously detecting, on the same solid phase, anti-HCV capsid antibodies and HCV capsid antigen. Thus, the depositing onto the solid phase, for the purpose of detecting anti-HCV capsid antibodies, of a capsid antigen which has the same epitopes as those recognized by the labeled anti-HCV capsid antibody or antibodies used for the purpose of detecting the capsid antigen leads to attachment of labeled antibody or antibodies to the solid phase and results in the assay giving a falsely positive response.

In order to bypass this risk of interference, Chiron Corp. has performed assays detecting the capsid antigen and only the anti-NS3/NS4 antibodies of patients. For this, Chiron used, firstly, an NS3/4a antigen attached to a solid phase, to capture the anti-HCV antibodies of the sample tested, and, secondly, monoclonal anti-HCV capsid antibodies (c11-3 and c11-7), also attached. The captured antibodies were detected using an antigen fused with SOD (superoxide dismutase) in the presence of a peroxidase-labeled monoclonal antibody, while the captured antigen was detected using another monoclonal antibody also labeled with peroxidase (VII European Congress of the International Society of Blood Transfusion—Paris, Jul. 15-18, 2001).

Faced with the interference problem, application EP 1 020 727 (Advanced Life Science Institute) provides a method for simultaneously measuring the HCV capsid antigen and the anti-HCV capsid antibodies (a "combo" type assay), in which the antigen is captured and labeled by antibodies directed against capsid epitopes different from the capsid epitopes used simultaneously to capture and reveal or detect anti-capsid antibodies. A representative example is given where, in the simultaneous assay for detecting the antigen by sandwich and the antibodies by indirect assay, use is made, for detecting the antigen, of a first antibody (capture antibody), directed against the epitopes of the sequence of amino acid (AA) 100 to amino acid 130 of the HCV capsid, and a second antibody (detection antibody), directed against the epitopes of the sequence AA40-50 and, for detecting the antibodies, the capture antigen used contains, itself, the sequences AA1-42 and AA66-80.

This method is not, however, free of drawbacks, in particular because it requires the use of antibodies directed against epitopes which are relatively distant from one another, and which are in fact minor, relatively nonimmunogenic epitopes. It also has the drawback, due to the absence of the sequence A43-65, of not detecting the antibodies directed against this last sequence and therefore of losing sensitivity.

In addition, it captures the capsid antigen and captures the anti-capsid antibodies via two regions of the capsid protein which are clearly distinct, i.e. not superimposed (AA 1-42 and AA 66-80 for detecting the antibodies and AA 100-130 for detecting the antigen) unlike the present invention.

Figure 2:
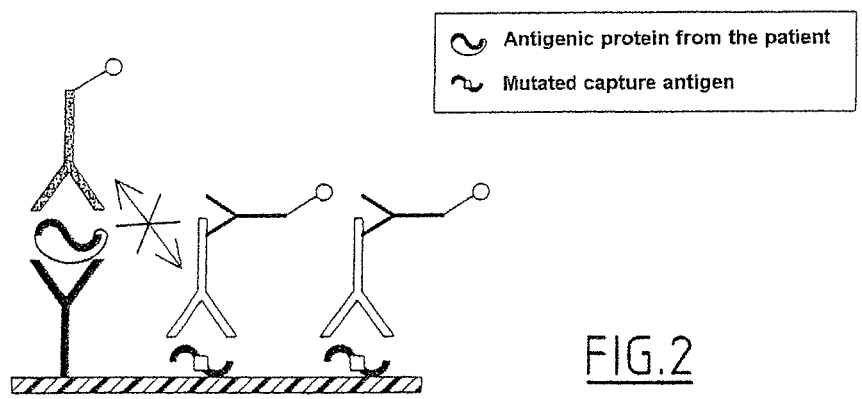

Patent application WO 01/96875 A2 (Chiron) describes, inter alia, an assay for simultaneously detecting the capsid and the anti-NS3 and -NS4 antibodies (an "incomplete combo", FIG. 2) which makes use of N-lauryl sarcosine as detergent. On the other hand, it mentions, very summarily, in FIG. 8 and page 33, a "complete combo" assay, i.e. an assay for simultaneously detecting the capsid antigen (by sandwich) and the anti-HCV capsid and anti-HCV nonstructural protein antibodies (by double antigen sandwich). To capture the antigen, two antibodies, c11-3 and c11-7, reputed to recognize a vast N-terminal Portion (AA 10-53) of the HCV capsid are used, and, for the detection, a third antibody, c11-14, reputed to recognize a C-terminal portion (AA 120-130) of the HCV capsid is used. To detect the antibodies, the capture antigen used is a fusion antigen with multiple epitopes ("MEFA 12", see Table 2 of application WO 01/96875) which contains, as a fusion with a fragment of superoxide dismutase (SOD), NS3, NS4 and NS5 antigens and series of capsid sequences of several HCV strains: AA 9-53, carrying the mutation R47L, AA 64-88 and AA 67-84. The sequences AA 54-63 and AA 54-66 are absent from these two series of sequence.

However, the real implementation of the "complete combo" assay of patent application WO 01/96875 A2 is not described. It is therefore impossible for those skilled in the art to clearly and unambiguously determine whether the combo assay of FIG. 8 can function, even less whether it can satisfy the problem posed, i.e. to detect as early as possible infection with HCV. In any event, it is clear that, in the best case scenario, the combo of patent application WO 01/96875 A2 would inevitably lose the detection of all the antibodies directed against the missing sequences AA 54-63 and AA 54-66. A risk of loss of sensitivity would ensue.

Patent application EP 1 251 353 A2 (Ortho-Clinical Diagnostics) describes a "complete combo" assay using the same antibodies for detecting the capsid, without however specifying their origin or their epitope specificity. In addition, it specifies that the detergent used is a detergent of the BRIJ or MYRJ type, which apparently is preferred to the N-lauryl sarcosine of the capsid antigen detection kit marketed by, Ortho Clinical Diagnostics (see Example 3 [0012]). The anti-capsid antibodies are detected using a capsid antigen which has been modified (by mutagenesis): C22KSN∀47,48 (protein from fusion with SOD comprising the capsid sequence AA 10-99 deleted of amino acids 47 and 48) or C22KSR47L (protein from fusion with SOD comprising the capsid sequence AA 10-99, with a leucine replacing an arginine in position 47).

Patent application WO 03/002 749 A2 (Abbott) describes many antigens and assays for detecting HCV capsid antigen. The only "complete combo" assay which it describes—referred to as "Real Combo" (FIG. 1, and page 59)—makes use, for detecting the anti-capsid antibodies, of a biotinylated peptide corresponding to amino acids 11-28 of the capsid, immobilized in solid phase. To detect the capsid, it uses the combination of antibodies from Advanced Life Science Institute C11-14 (recognizing the capsid sequence AA 45-50) in solid Phase and C11-10 (recognizing the capsid sequence AA 32-36) labeled with acridine. Application WO 03/002 749 A2 therefore effects the capture of the capsid antigen and the capture of the anti-capsid antibodies via two clearly distinct, i.e. not superimposed, capsid sites (AA 11-28 to detect the antibodies and AA 45-50 to detect the antigen), unlike the present invention.

The authors of the present invention have therefore endeavored to develop an alternative method in order to solve the problem posed.

A method for simultaneously detecting an HCV antigen and a patient's antibodies directed against this antigen has now been found which avoids this problem of interference and which attains levels of sensitivity and of earliness of detection which are close to those of PCR, while at the same time making it possible to follow the serological evolution of the patient after seroconversion.

The authors of the invention solve this problem by making certain epitopes of the target antigens used to capture the antibodies artificially different by structural modification. The epitopes thus modified are then destroyed. Simultaneously, the antibodies used to capture and/or detect the antigens are themselves selected such that they precisely recognize unmodified epitopes present on the patient's antigens, and such that they thus cannot bind to the modified antigens, which no longer exhibit these same epitopes. Since the epitopes are no longer identical, there is therefore no longer any competition between the antibodies used to capture and/or detect the HCV antigen, and the patient's antibodies. Contrary to a certain number of techniques of the prior art, the capture of the capsid antigen and that of the anti-capsid antibodies can take place on a single and same protein region of the capsid and will avoid the loss of detection of a certain number of anti-capsid antibodies, as will be seen later.

Since multiple epitopes have been identified in the N-terminal portion of the capsid, this protein region is the most suitable for obtaining both very sensitive detection of the capsid antigen and of the anti-capsid antibodies.

By virtue of the present invention, it is possible to use, simultaneously for detecting the antibodies and the antigens, the most immunoreactive sequences and thus to increase the sensitivity of the detection.

It goes without saying that the invention is not limited to the detection of only infection due to the hepatitis C virus (HCV). It also encompasses the generalization of the method, of the reagents and of the kits described below to the detection of infection, and/or the monitoring of infection, due to any sort of infectious microorganisms (for instance viruses, such as, for example, the viruses responsible for the various types of hepatitis A, B, C, D or E, retro-viruses, in particular the retroviruses responsible for AIDS in humans (HIV-1, HIV-1 group O, HIV-2) or monkeys, the cytomegalovirus (CMV), flaviviruses, including the dengue viruses, and also bacteria, microbial parasites, etc.) for which simultaneous detection of antigens and of antibodies is desirable. The invention, more particularly described herein for the hepatitis C virus (HCV) is of a very general scope which those skilled in the art will easily understand.

Definitions

The term "hepatitis C virus" or "HCV" herein covers all the strains and all the types, subtypes and genotypes of the virus responsible for hepatitis C. The method of the invention in fact aims to detect any infection with HCV, whatever its origin and its genotype. This comprises in particular the well known types and subtypes of the virus circulating in Europe, in the United States, in Japan, etc. (i.e. the 6 major genotypes: 1, 2, 3, 4, 5 and 6, and their subtypes 1a, 1b, 3a, etc.). See Stuyver et al. (1994); Bukh (1995).

The term "human immunodeficiency virus" or "HIV" is intended to mean all the strains and all the types, subtypes, groups and genotypes of the retrovirus responsible for AIDS in humans The term HIV includes in particular the HIVs-1 (HIV-1 group M, HIV-1 group O), and the HIVs-2 and their variants.

In the context of the invention, a "biological sample" preferably consists of a biological fluid, such as blood, plasma, serum, urine, cerebrospinal fluid, saliva, etc.

The term "antibody" refers to any whole antibody or functional fragment of an antibody comprising or consisting of at least one antigenic combination site making it possible for said antibody to bind to at least one antigenic determinant of an antigenic compound. By way of example of antibody fragments, mention may be made of Fab, Fab' and $F(ab')_2$ fragments and also scFv (single chain variable fragment) chains, dsFv (double-stranded variable fragment) chains, etc. These functional fragments can in particular be obtained by genetic engineering.

The production Of monoclonal antibodies or of monospecific polyclonal sera which are of use in the context of the invention is the result of conventional techniques, details of which are given later.

The term "capture antibody" is intended to mean an antibody or a part of an antibody, preferably attached to a solid phase, which is capable of retaining an antigen of the microorganism, for example of HCV or of an HIV, present in a biological sample, by affinity binding.

The presence of the antibodies and antigens in the biological sample is revealed by "detection means". As regards the detection of the antigen, the invention in particular provides detection using at least one "detection antibody". Such a detection antibody, which is labeled, is capable of binding to the captured antigen, by affinity binding, by recognizing an epitope site which is different from that recognized by the capture antibody or identical due to the presence of a repeat motif in the capsid. As regards the detection of the antibodies, use may in particular be made of labeled anti-immunoglobulin or anti-isotype antibodies, for example anti-immunoglobulins G.

The term "labeled" refers both to direct labeling (via enzymes, radioisotopes, fluorochromes, luminescent compounds, etc.) and to indirect labeling (for example via antibodies which are themselves labeled directly or using reagents consisting of a labeled "affinity pair", such as, but not exclusively, the pair labeled avidin-biotin, etc.).

The term "antigenic fragment" is intended to mean all or part of a natural or recombined protein of an infectious microorganism, such as the hepatitis C virus or HIV, capable of inducing antibody synthesis, in an infected patient or in an immunized animal. It may in particular be all or part of the capsid protein, or of the nonstructural proteins of HCV, in particular NS3 and NS4, whether or not they are obtained by genetic engineering. It may also be all or part of a protein encoded by the gag gene of an HIV, in particular P25 (HIV-1) or P26 (HIV-2), or of a protein encoded by the envelope gene, in particular gp41 (HIV-1) or gp36 (HIV-2).

The term "capture antigen" is intended to be an isolated antigenic fragment, preferably attached to a solid phase, which is capable of being recognized by antibodies directed against the microorganism, such as anti-HCV or anti-HIV antibodies, and of allowing affinity binding with the latter.

The term "detection antigen" is intended to mean a labeled and modified antigen like the capture antigen (i.e. it contains at least one epitope site or epitope which has been destroyed). It makes it possible either to detect the captured antigen by competition or to detect antibodies by the conventional antigen-antibody-antigen sandwich method, also called "double antigen sandwich" method (Maiolini et al. (1978)).

In accordance with the present invention, the capture antigen, and/or the detection antigen optionally used, in particular in antibody detection by antigen-antibody-antigen sandwich, contains at least one epitope site or epitope which has been destroyed. An "epitope site" or "epitope" is a sequence of amino acids which is recognized by an antibody and allows specific binding thereof.

As regards the HCV proteins, several epitopes of the capsid protein have been identified. The epitopes located between amino acid 16 and amino acid 40, and between amino acid 44 and amino acid 47, are in particular known. Reference may also be made, for example, to the articles or disclosures Okamoto et al. (1990); Nasoff et al. (1991); Leahy et al. (1991); Takahashi et al. (1992); Sällberg et al. (1992); and Ishida (1993).

Many epitopes of nonstructural proteins of HCV are also known to those skilled in the art. On the NS3 protein, the epitopes located between amino acid 1188 and amino acid 1493 (Yang et al. (1995)), and between amino acid 1175 and amino acid 1334 (Yang et al. (1999)), and an epitope between amino acid 1460 and amino acid 1532 (Clayes et al. (1995)), are known.

One of the most widely known NS4 epitopes, the epitope 5-1-1 (AA 1689-1706), is mentioned in Cerino et al. (1991).

As regards HIV, several epitopes have also been described in the prior art. They are in particular epitopes of the HIV-1 (group M) P25 protein, located between amino acids 293 and 350, but also the immunodominant epitope of gp41 described by Gnann et al. (1987) or a variant of this sequence; this is again an epitope of the P26 protein, in particular an epitope with a sequence homologous to that of the epitope of HIV-1 P25 described above, for example, or an epitope of HIV-2 gp36, in particular the immunodominant epitope of gp36 described by Gnann et al. (1987), or a variant of this sequence.

The expression epitope site or epitope "which has been destroyed" is intended to mean that said epitope site or epitope is modified within its structure (primary, secondary, tertiary and/or quaternary) in such a way that the capture antigen, or detection antigen, which comprises this destroyed epitope may not bind to the capture antibody, and/or to the detection antibody, directed against the antigen detected simultaneously, while at the same time conserving the ability to bind the antibodies directed against the microorganism, such as the anti-HCV or anti-HIV antibodies, possibly present in the biological sample, by recognizing other epitope sites which have remained intact. Consequently, the capture and/or detection antibodies are selected so as to specifically recognize the epitope in question in its "intact" form, i.e. "non-destroyed" or "native" form, on the antigen present in the biological sample. In the context of the present invention, this epitope in its intact form is also called epitope "homologous" to the destroyed epitope.

The term "specifically", when it refers to specific recognition or binding of an antibody with respect to an antigen, means that the antibody interacts with the antigen without any substantial interaction with other antigens, or, if it is a question of "specific" recognition with an epitope, by virtually exclusive recognition of this epitope. Association constants greater than $10^8$ L·mol$^{-1}$ are preferable.

Capture and Detection Antibodies

The antibodies used in the present invention are antibodies specific for the antigen and, for this reason, are monoclonal antibodies or monospecific polyclonal antibodies, that is to say they recognize specifically only one epitope.

The monoclonal antibodies can be obtained according to the conventional method of lymphocyte fusion and hybridoma culture described by Köhler and Milstein, (1975). Other methods for preparing monoclonal antibodies are also known (Harlow et al. (1988)). The monoclonal antibodies can be prepared by immunizing a mammal (for example a mouse, a rat, a rabbit, or even a human, etc.) and using the lymphocyte fusion technique resulting in hybridomas (Köhler and Milstein, (1975)).

Techniques which are an alternative to this usual technique exist. It is possible, for example, to produce monoclonal antibodies by expression of a nucleic acid which has been cloned using a hybridoma. It is also possible to produce antibodies using the Phage display technique, by introducing antibody cDNAs into vectors, which are typically filamentous phages (for example fUSE5 for *E. coli*, Scott et al. (1990)). The latter constitute libraries and exhibit scFv fragments at their surface. Protocols for constructing these antibody libraries are described in Marks et al. (1991).

Polyclonal antibodies can be obtained from the serum of an animal immunized against an antigen which is peptide in nature, according to the usual procedures.

In general, a polypeptide, in particular a recombined Polypeptide, or an oligopeptide may, for example, be used as immunogen. According to a conventional protocol, rabbits are immunized with the equivalent of 1 mg of the peptide immunogen according to the procedure described by Benoit et al. (1982). At four-week intervals, the animals are given injections of 200 μg of antigen and bled 10 to 14 days later. After the third injection, the ability of the antiserum to bind to the antigenic peptide, radiolabeled with iodine, prepared by the chloramine-T method, is evaluated. It is then purified by chromatography on an ion exchange column consisting of carboxymethylcellulose (CMC). The antibody molecules collected by elution are then adjusted to the desired concentration by methods well known to those skilled in the art, for example using DEAF Sephadex to obtain the IgG fraction.

In order to increase the specificity of the polyclonal serum, the antibodies can be purified by immunoaffinity chromatography (or immunoadsorption chromatography) using peptides (such as capsid peptides AA 16-44 and AA 39-74 of HCV, by way of nonlimiting example) which were used for the immunization and which were immobilized in solid phase. The antiserum is brought into contact with such a peptide immobilized in solid phase for a sufficient period of time so as to immunoreact the peptide with the antibody molecule in order to form an immunocomplex in solid phase.

The inventors have thus more particularly used the specific anti-HCV antibodies indicated in Table 1 below.

TABLE 1

| Monoclonal antibody | Class | Natural epitope recognized |
|---|---|---|
| mAb 1 | IgG2a | $^{44}$LGVR$^{47}$ (SEQ ID No. 19) |
| mAb 2 | IgG2a | $^{30}$IVGGVYL$^{36}$ (SEQ ID No. 20) |
| mAb 3 | IgG1 | $^{29}$QIVGGV$^{34}$ (SEQ ID No. 21) |
| mAb 4 | IgG1 | $^{29}$QIVGGV$^{34}$ (SEQ ID No. 21) |
| mAb 5 | IgG1 | $^{30}$IVGGVYL$^{36}$ (SEQ ID No. 20) |
| mAb 6 | IgG1 | $^{30}$IVGGVYL$^{36}$ (SEQ ID No. 20) |

As regards the Combo assay for detecting HIV, the antibody used is preferentially a monoclonal antibody which recognizes one of the following polypeptide sequences, or the corresponding sequence of a variant HIV strain:

epitope of the P25 protein of an HIV-1 group M of sequence 308QASQEVKNWMTETLL322 (SEQ ID No. 24);

epitope of the P26 protein, in particular an epitope of sequence homologous to that of the epitope of HIV-1 P25 described by the sequence identifier SEQ ID No. 24, such as, for example, an epitope containing the sequence QTDPAVKNWMTQTLL (SEQ ID No. 25) (HIV-2 isolate: ROD).

It goes without saying that it is within the scope of those skilled in the art to produce or to obtain monoclonal antibodies of epitope specificity similar or identical to that described for the antibodies above, and which are suitable for implementing the present invention.

Capture and/or Detection Antigens

The capture antigen, and/or the detection antigen, used in the invention contains at least one epitope site which has been destroyed. The destruction of at least two sites on the antigen may be necessary, when two different antibodies, which both risk interacting with the capture antigen and/or the detection antigen, are used. This is the case, for example, for sandwich-type immunoassays, which use a capture antibody immobilized on the same surface as the capture antigen, and a detection antibody. The capture antibody is then selected in such a way that it specifically recognizes an epitope, on the natural antigen of the patient, homologous to one of the two destroyed epitopes on the capture antigen, while the detection antibody is selected in such a way that it specifically recognizes an epitope, on the natural antigen of the patient, homologous to the other of the two destroyed epitopes on the capture antigen.

The capture antigen and/or the detection antigen may comprise or consist of a peptide which mimics all or part of an epitope derived from an antigenic protein of the microorganism, in particular of HCV or of an HIV.

Preferably, it is a peptide of the capsid protein, detection of the anti-capsid antibodies being particularly advantageous, in particular in the case of chronic hepatitis, where very few antigens are seen and it is more the circulating anti-capsid antibodies which are observed. It may also be (a) peptide(s) of a nonstructural protein, such as NS3 and/or NS4. Various capture or detection antigens can also be combined together. This embodiment, which uses several different capture and/or detection antigens, makes it possible, for example, to simultaneously detect anti-capsid antibodies and antibodies against nonstructural proteins NS3 and/or NS4 of HCV. Simultaneous detection of the anti-capsid antibodies and of the anti-NS3 antibodies is particularly preferred. The invention also comprises simultaneous detection of capsid antigens, of anti-capsid antibodies, of antibodies against E1 and/or E2 envelope structural proteins, of E1 and/or E2 envelope antigen, and/or of antibodies against nonstructural proteins NS3 and/or NS4 of HCV. Other combinations which can be envisioned are also part of the invention.

In the same way, the simultaneous detection of gag antigen, of antibodies against gag and/or antibodies against envelope of the AIDS virus (HIV-1, HIV-2, etc.), the sequences of which have been published in the articles Wain-Hobson et al. (1985); Ratner et al. (1985); Sanchez-Pescador et al. (1985); Guyader et al. (1987), is also part of the invention. Preferentially, the gag antigen to be detected is the HIV-1 P25 protein or HIV-2 P26 and the anti-gag antibodies sought are directed against these proteins. Still preferentially, the envelope antigens for detecting the antibodies against envelope of HIV-1 and of HIV-2 are HIV-1 gp41 and HIV-2 gp36.

Similarly, the detection of NS1 antigen, described by Alcon et al. (2002), simultaneously to that of antibodies against NS1, or even also of antibodies against NS2, NS3 and/or S4 of the dengue viruses, is also part of the invention.

The techniques for application are well known to those skilled in the art.

Preferentially, since it is more practical, the capture and/or detection antigens are synthetic peptides Produced by the standard techniques well known to those skilled in the art. By way of example, mention may be made of synthesis of the Merrifield type which is advantageous for reasons of purity, of antigenic specificity, and of lack of unwanted by-products, and for its ease of use (Merrifield, (1963); R. C. Sheppard (1971); Atherton et al. (1989)). As automatic synthesizer, use may be made of the "9050 Plus Pep Synthesizer" from Millipore, the "Pioneer" synthesizer from Perseptive, the "433A" synthesizer from ABI (Applied Biosystems Inc.) or the "Symphony" synthesizer from Rainin. The peptides can also be obtained by homogeneous phase synthesis.

The destruction of the epitopes on these capture and/or detection antigens can be carried out in various ways. The only condition required for this modification of the epitope sites is that the capture and/or detection antigen may not bind to the capture antibody and/or to the detection antibody, but at the same time substantially conserves the ability to bind the antibodies directed against the microorganism, in particular anti-HCV or anti-HIV antibodies, possibly present in the biological sample.

Modification of at least one amino acid, preferably two amino acids, in each epitope site targeted, may be sufficient to destroy the epitope without, however, destabilizing the other unmodified epitopes. Such a modification may in particular be obtained by an amino acid substitution, for example by substituting a non-glycine residue with a glycine or alanine residue, or by substituting an amino acid of one class with an amino acid of another class. It is possible, for example, to substitute an amino acid with a polar side chain (such as asparagine, glutamine, serine, threonine or tyrosine) with an amino acid with a nonpolar side chain (such as glycine, alanine, valine, leucine, isoleucine, phenylalanine, methionine, tryptophan or cysteine), and vice versa. It is also possible to substitute an amino acid with a basic side chain (such as lysine, arginine or histidine) with an amino acid with an acid side chain (such as aspartic acid or glutamic acid), and vice versa, or else to substitute an amino acid in which the side chain bears a ring (for example tyrosine or phenylalanine) with an amino acid with a linear side chain, and vice versa. A deletion of one or more amino acids, or an insertion of one or more amino acids, in particular of unnatural amino acids, in the epitope, also makes it possible to destroy the epitope. Modifications of the functional groups of the amino acids, namely in particular the groups OH, $NH_2$ or SH, are also possible.

Among the peptides of use in the context of the present invention, it is possible to imagine peptides derived from all sorts of infectious microorganisms (for instance viruses, such as, for example, the viruses responsible for the various types of hepatitis, retro-viruses, in particular the retroviruses responsible for AIDS (HIV-1, HIV-2, etc.), the CMV virus, the dengue viruses, and also bacteria, microbial parasites, etc.) for which simultaneous detection of antigens and of antibodies is desirable.

In particular, and by way of nonexclusive illustration, mention may in particular be made of the HCV capsid peptides, more particularly those ranging from amino acids 1 to 75, 6 to 68 and 1 to 53. These sequences, which correspond to consensus sequences of genotype 1 (subtypes 1a, 1b, 1c) are given in the attached sequence listing and denoted, respectively, SEQ ID No. 1, No. 2 and No. 3:

SEQ ID No. 1
$_1$MSTNPKPQRKTKRNTNRRPQDVKFPGGGQIV$_{31}$GGV$_{34}$YL$_{36}$LPRRGPR

L$_{44}$GVR$_{47}$ATRKTSERSQPRGRRQPIPKARRPEGRS$_{75}$

SEQ ID No. 2
$_6$KPQRKTKRNTNRRPQDVKFPGGGQIV$_{31}$GGV$_{34}$YL$_{36}$LPRRGPRL$_{44}$GV

R$_{47}$ATRKTSERSQPRGRRQP1PKA$_{68}$

SEQ ID No. 3
$_1$MSTNPKPQRKTKRNTNRRPQDVKFPGGGQIV$_{31}$GGV$_{34}$YL$_{36}$LPRRGPR

L$_{44}$GVR$_{47}$ATRKTS$_{53}$

In the same way, a peptide or polypeptide which is of use in the context of the present invention is a gag polypeptide or an envelope polypeptide of HIV.

It is in particular a peptide corresponding to the consensus sequence of the HIV-1 P25 protein, the sequence of which is denoted by the sequence identifier SEQ ID No. 23 in the attached sequence listing.

SEQ ID No. 23
$_{293}$FRDYVDRFYKTLRAEQASQEVKNWMTETLLVQNANPDCKTILKALGP

AATLEEMMTAC$_{350}$

It may also be a peptide comprising an epitope of gp41 of an HIV-1, in particular a peptide of sequence SEQ ID No. 26 to SEQ ID No. 31:

SEQ ID No. 26:
LGLWGCSGKLIC,

SEQ ID No. 27:
LGIWGCSGKLIC,

SEQ ID No. 28:
LGLWGCSGKHIC,

SEQ ID No. 29:
LGMWGCSGKHIC

SEQ ID No. 30:
RILAVERYLKDQQLLGIWGCSGKLIC

SEQ ID No. 31:
RILAVERYLKDQQLLGIWGSGKLICTTAVPWNAS.

The use of a gag polypeptide or an envelope polypeptide of an HIV-2 as capture and/or detection antigen is also part of the present invention. It is in particular a polypeptide of gp36, of sequence SEQ ID No. 32 or SEQ ID No. 33 as follows:

SEQ ID No. 32:
LNSWGCAFRQVC,

SEQ ID No. 33:
RVTAIEKYLQDQARLNSWGCAFRQVCHTTVPWVNDS.

It may also be a polypeptide of the P26 protein of an HIV-2, for example a polypeptide of sequence homologous to that of the polypeptide of the P25 protein described by the sequence identifier SEQ ID No. 23.

Modified peptides or polypeptides, which are of use as capture and/or detection antigens, are also part of the invention. They may in particular be capsid peptide fragments bearing at least one modified epitope site. A subject of the invention is therefore a peptide or polypeptide derived from the HCV capsid protein, bearing at least one intact epitope site and at least one destroyed epitope site, said destroyed epitope site thus being made incapable of being recognized by an anti-capsid antibody. Preferred peptides exhibit a substitution of two, three or four amino acids, in particular in the portion consisting of amino acids 20 to 40 and in the portion consisting of amino acids 44 to 47. The following mutations are particularly advantageous and preferred:

substitution of amino acids 34, 44 and 47 with glycine residues (sequence SEQ ID No. 4, peptide denoted "Cap 1-75 (G34-G44-G47)"):

SEQ ID No. 4:
Cap 1-75 (G34-G44-G47)
$_1$MSTNPKPQRKTKRNTNRRPQDVKFPGGGQIV$_{31}$GGG$_{34}$YL$_{36}$LPRRGPR

G$_{44}$GVG$_{47}$ATRKTSERSQPRGRRQPIPKARRPEGRS$_{75}$ substitution of amino acids 31, 44 and 47 with glycine residues (sequence SEQ ID No. 5, peptide denoted "Cap 1-75 (G31-G44-G47)"):

SEQ ID No. 5:
Cap 1-75 (G31-G44-G47)
$_1$MSTNPKPQRKTKRNTNRRPQDVKFPGGGQIG$_{31}$GGV$_{34}$YL$_{36}$LPRRGPR

G$_{44}$GVG$_{47}$ATRKTSERSQPRGRRQPIPKARRPEGRS$_{75}$ substitution of amino acids 36, 44 and 47 with glycine residues (sequence SEQ ID No. 6, peptide denoted "Cap 1-75 (G36-G44-G47)"):

SEQ ID No. 6:
Cap 1-75 (G36-G44-G47)
$_1$MSTNPKPQRKTKRNTNRRPQDVKFPGGGQIV$_{31}$GGV$_{34}$YG$_{36}$LPRRGPR

G$_{44}$GVG$_{47}$ATRKTSERSQPRGRRQPIPKARRPEGRS$_{75}$ substitution of amino acids 34, 44 and 47 with glycine residues (sequence SEQ ID No. 7, peptide denoted "Cap 6-68 (G34-G44-G47)"):

SEQ ID No. 7:
Cap 6-68 (G34-G44-G47)
$_6$KPQRKTKRNTNRRPCOVKFPGGGQIV$_{31}$GGG$_{34}$YL$_{35}$LPRRGPRG$_{44}$GV

G$_{47}$ATRKTSERSQPRGRRQPIPKA$_{68}$ substitution of amino acids 31, 44 and 47 with glycine residues (sequence SEQ ID No. 8, peptide denoted "Cap 6-68 (G31-G44-G47)"):

SEQ ID No. 8:
Cap 6-68 (G31-G44-G47)
$_6$KPQRKTKRNTNRRPQDVKFPGGGQIG$_{31}$GGV$_{34}$YL$_{36}$LPRRGPRG$_{44}$GV

G$_{47}$ATRKTSERSQPRGRRQPIPKA$_{68}$ substitution of amino acids 36, 44 and 47 with glycine residues (sequence SEQ ID No. 9, peptide denoted "Cap 6-68 (G36-G44-G47)"):

SEQ ID No. 9:
Cap 6-68 (G36-G44-G47)
$_6$KPQRKTKRNTNRRPQDVKFPGGGQIV$_{31}$GGV$_{34}$YG$_{36}$LPRRGPRG$_{44}$GV

G$_{47}$ATRKTSERSQPRGRRQPIPKARRPEGRS$_{75}$ substitution of amino acids 34, 44 and 47 with glycine residues (sequence SEQ ID No. 10, peptide denoted "Cap 1-53 (G34-G44-G47)"):

SEQ ID No. 10:
Cap 1-53 (G34-G44-G47)
$_1$MSTNPKPQRKTKRNTNRRPQDVKFPGGGQIV$_{31}$GGG$_{34}$YL$_{36}$LPRR

GPRG$_{44}$GVG$_{47}$ATRKTS$_{53}$ substitution of amino acids 31, 44 and 47 with glycine residues (sequence SEQ ID No. 11, peptide denoted "Cap 1-53 (G31-G44-G47)"):

SEQ ID No. 11:
Cap 1-53 (G31-G44-G47)
$_1$MSTNPKPQRKTKRNTNRRPQDVKFPGGGQIG$_{31}$GGV$_{34}$YL$_{36}$LPR

RGPRG$_{44}$GVG$_{47}$ATRKTS$_{53}$ substitution of amino acids 36, 44 and 47 with glycine residues (sequence SEQ ID No. 12, peptide denoted "Cap 1-53 (G36-G44-G47)"):

SEQ ID No. 12:
Cap 1-53 (G36-G44-G47)
$_1$MSTNPKPQRKTKRNTNRRPQDVKFPGGGQIV$_{31}$GGV$_{34}$YG$_{36}$LPRR

GPRG$_{44}$GVG$_{47}$ATRKTS$_{53}$ deletion of amino acids 45 and 46:

SEQ ID No. 13:
Cap 1-75 (G34-del(45-46))
$_1$MSTNPKPQRKTKRNTNRRPQDVKFPGGGQIV$_{31}$GGG$_{34}$YL$_{36}$LPRR

GPRL$_{44}$-R$_{47}$ATRKTSERSQPRGRRQPIPKARRPEGRS$_{75}$ modification of the backbone length:

SEQ ID No. 14:
Cap 1-75 (G34-βA45)
$_1$MSTNPKPQRKTKRNTNRRPQDVKFPGGGQIV$_{31}$GGG$_{34}$YL$_{36}$LPRR

GPRL$_{44}$βA$_{45}$VR$_{47}$ATRKTSERSQPRGRRQPIPKARRPEGRS$_{75}$ where βA represents β-alanine modification of the backbone length by amino acid insertion and mutations:

SEQ ID No. 15:
Cap 1-75 (G34-G46-G46')
$_1$MSTNPKPQRKTKRNTNRRPQDVKFPGGGQIV$_{31}$GGG$_{34}$YL$_{36}$LPRR

GPRL$_{44}$G$_{45}$G$_{46}$G$_{46'}$R$_{47}$ATRKTSERSQPRGRRQPIPKARRPEGRS$_{75}$ inversion of polarity:

SEQ ID No. 16:
Cap 1-75 (nL29-G30-G44-G47)
$_1$MSTNPKPQRKTKRNTNRRPQDVKFPGGGnL$_{29}$G$_{30}$V$_{31}$GGVYL$_{36}$LP

RRGPRG$_{44}$GVG$_{47}$ATRKTSERSQPRGRRQPIPKARRPEGRS$_{75}$ where nL represents norLeucine
amino acid substitution SEQ ID No. 17:
Cap 1-75 (G34-F35-G44-G47)
$_1$MSTNPKPQRKTKRNTNRRPQDVKFPGGGQIV$_{31}$GGG$_{34}$F$_{35}$L$_{36}$LPR

RGPRG$_{44}$GVG$_{47}$ATRKTSERSQPRGRRQPIPKARRPEGRS$_{75}$ amino acid substitution SEQ ID No. 18:
Cap 1-75 (G34-hS35-G44-G47)
$_1$MSTNPKPQRKTKRNTNRRPQDVKFPGGGQIV$_{31}$GGG$_{34}$hS$_{35}$L$_{36}$LPR

RGPRG$_{44}$GVG$_{47}$ATRKTSERSQPRGRRQPIPKARRPEGRS$_{75}$ where hS represents homoSerine.

The invention also relates to a peptide or polypeptide derived from a gag protein of an HIV, bearing at least one intact epitope site and at least one destroyed epitope site, said destroyed epitope site thus being made incapable of being recognized by an antibody directed against the same gag protein. More particularly, said polypeptide comprises a consensus sequence of the HIV-1 P25 protein and may exhibit a substitution of one, two, three, four or five amino acids, in particular in the portion consisting of amino acids 293 to 322. Preferentially, said modified polypeptide has the consensus sequence of the HIV-1 (M) P25 protein in which amino acids 295, 298, 310 and 312 have been substituted with a glycine residue, and amino acid 316 has been substituted with a phenylalanine residue:

(SEQ ID No.22)
$_{293}$FRGYVGRFYKTLRAEQAGQGVKNFMTETLLVQNANPDCKTILKALG

PAATLEEMMTAC$_{350}$

When these peptide sequences are used, it may be advantageous to add, in the N-terminal position, the amino acids C-G-G- (i.e. Cys-Gly-Gly-) in order to be able to attach them more readily to a support or any molecule of interest. The peptide C-G-G-Cap 1-75 (G34-G44-G47) is particularly advantageous in this regard.

Methods of Detection

The invention provides, in general, a method for detecting, in vitro, an infection with a microorganism in a biological sample, comprising the simultaneous detection of an antigen of said microorganism and of an antibody directed against said microorganism, present in a biological sample, which method comprises
a) bringing the biological sample into contact with a capture antibody directed against said micro-organism, and a capture antigen derived from said microorganism;
b) incubating the mixture under conditions allowing the formation of antigen-antibody complexes;
c) revealing the antigen-antibody complexes formed which optionally uses at least one labeled detection antibody capable of binding to the antigen of said microorganism which has been captured and/or optionally also a labeled detection antigen capable of binding to the antibody directed against said microorganism which has been captured;

and in which the capture antigen of said micro-organism comprises, or is, an antigenic fragment of said microorganism in which at least one epitope has been destroyed; and the capture and/or detection antibody recognizes said epitope, which is intact, of the antigen which has been captured.

It is understood that the method of the invention is not restricted to the use of a single antibody/antigen pair. It may be carried out using several different capture antibodies and several different capture antigens.

In particular, the invention therefore provides a method for detecting, in vitro, an infection with the hepatitis C virus (HCV) in a biological sample, comprising the simultaneous detection of an antigen of HCV and of an anti-HCV antibody directed against said antigen of HCV present in a biological sample, which method comprises a) bringing the biological sample into contact with an anti-HCV capture antibody and an HCV capture antigen;
b) incubating the mixture under conditions allowing the formation of antigen-antibody complexes;
c) revealing the antigen-antibody complexes formed, which optionally uses a labeled detection antibody capable of binding to the HCV antigen which has been captured and/or optionally a labeled detection antigen capable of binding to the anti-HCV antibody which has been captured;
and in which the HCV capture antigen comprises, or is, an antigenic fragment of HCV in which at least one epitope is destroyed;
and the capture and/or detection antibody recognizes said epitope, which is intact, of the antigen which has been captured.

The invention also provides a method for detecting, in vitro, an infection with a human immunodeficiency virus (HIV) in a biological sample, comprising the simultaneous detection of an antigen of an HIV and of an anti-HIV antibody directed against said antigen of HIV, present in a biological sample, which method comprises a) bringing the biological sample into contact with an anti-HIV capture antibody and an HIV capture antigen;
b) incubating the mixture under conditions allowing the formation of antigen-antibody complexes;
c) revealing the antigen-antibody complexes formed, which optionally uses a labeled detection antibody capable of binding to the HIV antigen which has been captured and/or optionally a labeled detection antigen capable of binding to the anti-HIV antibody which has been captured;
and in which the HIV capture antigen comprises, or is, an antigenic fragment of HIV in which at least one epitope has been destroyed;
and the capture and/or detection antibody recognizes said epitope, which is intact, of the antigen which has been captured.

Preferentially, said method allows the detection of an HIV-1, the detection of an HIV-2, or the detection both of an HIV-1 or of an HIV-2. Consequently, depending on the alternative considered, the HIV capture antigen used may comprise, or may be, an HIV-1 capture antigen, an HIV-2 capture antigen, and an HIV-1 and an HIV-2 capture antigen or a combination of an HIV-1 capture antigen and of an HIV-2 capture antigen, respectively.

The biological sample may optionally be treated in a prior step, or brought into contact with the capture antigen and the capture antibody under conditions which promote exposure of the antigens to be detected. Advantageously, the sample is treated with a denaturing agent, before detection, and preferably before it is brought into contact with the antibodies used. In the case of detection of the capsid of HCV, or of the gag protein of an HIV, this denaturing agent may in particular consist of one or more detergents of the nonionic type, such as, for example, Nonidet P-40 (NP40) (tert-octylphenoxy poly(oxyethylene) ethanol, also called IGEPAL CA630), or else of an acid solution.

This combined immunoassay may be carried out according to various formats well known to those skilled in the art: in solid phase or in homogeneous phase; in one step or in two steps; in a double sandwich method (sandwich for the two antigen and antibody detections); or in an indirect method (for the antibody detection) combined with a sandwich method (for the antigen detection), by way of nonlimiting examples.

According to a preferred embodiment, the capture antibody and the capture antigen are immobilized on a solid phase. By way of nonlimiting examples of solid phase, use may be made of microplates, in particular polystyrene microplates, such as those marketed by the company Nunc, Denmark. Use may also be made of solid particles or beads; paramagnetic beads, such as those provided by Dynal or Merck-Eurolab (France) (under the trade mark Estapor™), or else test tubes made of polystyrene or polypropylene, etc.

An immunoassay format of the type sandwiched between two antibodies (capture and detection antibodies) is particularly advantageous for detecting the antigens present in the biological sample, whereas the antibodies can be revealed using a capture antigen and a labeled conjugate which attaches to the antibody (according to a format commonly referred to as "indirect format"), for example labeled protein A or a labeled anti-immunoglobulin or anti-isotype antibody. The antibodies can also advantageously be detected using a capture antigen and a labeled antigen which attach to the antibody (according to a format referred to as "antigen-antibody-antigen sandwich" or "double antigen sandwich").

An immunoassay format for detecting the antigens by competition is also possible. Other modes of immunoassay can also be envisioned and are well known to those skilled in the art.

In general, according to the invention, the capture antibody and the detection antibody (in particular used in the case of the sandwich) are selected such that they recognize the natural target antigen to be detected, present in the biological sample, as an epitope, which is intact, homologous to the destroyed epitope on the capture antigen, and such that they do not recognize the destroyed epitope on the capture antigen.

The simultaneous detection of antigen of a micro-organism and of antibody directed against said micro-organism, in particular the simultaneous detection of the HCV antigen and of the anti-HCV antibodies, or else of the antigen of an HIV and of the anti-HIV antibodies, according to the invention, may be carried out in a single step, namely by simultaneously bringing the biological sample into contact with the detection means, such as in particular the detection antibody or antibodies, at the same time as the capture antibody or antibodies and the capture antigen(s). In this case, the immunoassay for detecting the antigen and the immunoassay for detecting the antibodies are both preferably carried out by sandwich. Alternatively, the detection means, such as in particular the detection antibody or antibodies, can be added to the mixture in a second step, i.e. after the first antigen-antibody complexes have formed. This is then described as a two-step assay.

As described above, the capture antigen may in particular be an antigenic fragment of the HCV capsid protein, in which at least one epitope site has been destroyed. The capture antigen may also consist of an antigenic fragment of a nonstructural protein of HCV, in particular, but not exclusively, of NS3 or of NS4, in which at least one epitope site has also been destroyed. Finally, the capture antigen may also consist of a combination of an antigenic fragment of the capsid protein, in which at least one epitope site has been destroyed, and of an antigenic fragment of a nonstructural protein of HCV, NS3 or NS4, in which at least one epitope site has also been destroyed. Any variant which can be envisioned by those skilled in the art is part of the invention.

According to a preferred embodiment of the invention, the method for detecting an infection with the hepatitis C virus (HCV) in a biological sample comprises:
a) bringing the sample into contact with an HCV capture antibody and an HCV capture antigen attached to a solid phase;
b) incubating the mixture under conditions allowing the formation of antigen-antibody complexes;
c) separating the solid phase and the liquid phase;
d) bringing the solid phase into contact with a labeled detection antibody capable of binding the HCV antigen which has been captured, and one or more labeled anti-immunoglobulin or anti-isotype antibodies capable of binding the anti-HCV antibody which has been captured,
the antigen for capturing anti-HCV antibodies comprising or being an antigenic fragment of the capsid protein of HCV, in which two epitopes have been destroyed,
and the capture and detection antibodies each recognizing one of said epitopes, which are intact, of the capsid antigen which has been captured.

According to another embodiment, the method of the invention allows the detection of an infection with an HIV, such as an HIV-1 or an HIV-2. Preferentially, said method comprises both a capture antigen derived from an HIV-1 and a capture antigen derived from an HIV-2, so as to be able to detect both anti-HIV-1 and anti-HIV-2 antibodies. According to this preferential mode, the method according to the invention can therefore be used, without distinction, to detect an infection with HIV-1 and/or HIV-2.

The capture antigen comprises at least one antigenic fragment of a gag protein of an HIV, for example of the HIV-1 P25 protein or of HIV-2 P26, in which at least one epitope site has been destroyed. The capture antigen may also comprise an antigenic fragment of an envelope protein of an HIV, in particular, but not exclusively, of HIV-1 gp41 or of HIV-2 gp36. Finally, the capture antigen may consist of a combination of antigenic fragments of a gag protein of HIV-1 and of HIV-2, supplemented, where appropriate, with antigenic fragments of an HIV-1 envelope protein and of an HIV-2 envelope protein. Any variant which can be envisioned by those skilled in the art is part of the invention.

According to a preferred embodiment of the invention, the method for detecting an infection with a human immunodeficiency virus (HIV) in a biological sample comprises:
a) bringing the sample into contact with an HIV capture antibody and an HIV capture antigen attached to a solid phase;
b) incubating the mixture under conditions allowing the formation of antigen-antibody complexes;
c) separating the solid phase and the liquid phase;
d) bringing the solid phase into contact with a labeled detection antibody capable of binding the HIV antigen which has been captured, and one or more labeled anti-immunoglobulin or anti-isotype antibodies capable of binding the anti-HIV antibody which has been captured,
the antigen for capturing anti-HIV antibodies comprising, or being, an antigenic fragment of the gag protein of HIV, in which at least one epitope has been destroyed,
and the capture and detection antibodies each recognizing one of said epitopes, which are intact, of the gag antigen which has been captured.

Preferentially, the method according to the invention is directed toward the detection of an infection either with HIV-1 or with HIV-2, or with HIV-1 and with HIV-2. According to the latter alternative, the antigen for capturing anti-HIV antibodies is the combination of a fragment of the gag protein of HIV-1 and of a fragment of the gag protein of HIV-2.

ELISA assays, radioimmunoassays, or any other detection technique, can be used to reveal the presence of the antigen-antibody complexes formed. The same type or several types of labels can be used to detect, firstly, the infectious microorganism antigen, in particular the HCV or HIV antigen, and, secondly, the antibody directed against the infectious microorganism, in particular the anti-HCV or anti-HIV antibody.

The detection of the presence of antigens or of antibodies in the biological sample can be completed by a quantification, for example by measuring the signals emitted by the labels (color, luminescence, radio-activity, etc.), according to the standard techniques known to those skilled in the art.

Kits

The kits and reagents which are of use for detecting an infection with a microorganism, such as the hepatitis C virus (HCV) or a human immunodeficiency virus (HIV), in a biological sample, in accordance with the method of the invention, can be provided such that the invention can be put into practice easily and in a manner applicable to many biological samples.

A subject of the invention is therefore a kit which is of use for detecting an infection with a microorganism in a biological sample, comprising:
a capture or detection antigen which comprises, or is, an antigenic fragment of a protein of a microorganism, said fragment comprising at least one destroyed epitope, while at the same time conserving the ability to bind the antibodies directed against the microorganism possibly present in the biological sample;
an antibody directed against said epitope, which is intact, of said protein of the microorganism.

Another particular subject of the invention is a kit for detecting an infection with the hepatitis C virus (HCV) in a biological sample, comprising:
a capture or detection antibody which comprises, or is, an antigenic fragment of a protein of HCV, said fragment comprising at least one destroyed epitope, while at the same time conserving the ability to bind the anti-HCV antibodies possibly present in a biological sample;
an antibody directed against said epitope, which is intact, of said protein of HCV, which is preferably an antibody for capturing said HCV antigen present in the biological sample.

Yet another subject of the invention is a kit for detecting an infection with a human immunodeficiency virus (HIV) in a biological sample, comprising:
a capture or detection antibody which comprises, or is, an antigenic fragment of a protein of HIV, said fragment comprising at least one destroyed epitope, while at the same time conserving the ability to bind the anti-HIV antibodies possibly present in a biological sample;

an antibody directed against said epitope, which is intact, of said protein of HIV, which is preferably an antibody for capturing said HIV antigen present in the biological sample.

Advantageously, this kit may contain several capture antigens and several capture antibodies.

As described above, the capture antibody and the capture antigen may advantageously be provided in a form immobilized on a solid phase, such as a microplate.

A preferred kit comprises a) the capture antigen which comprises, or is, an antigenic fragment of a protein of HCV, said fragment comprising at least two destroyed epitopes, while at the same time conserving the ability to bind the anti-HCV antibodies possibly present in a biological sample;

b) a capture antibody directed against one of said epitopes, which are intact, of said protein of HCV;

said capture antigen and said capture antibody being immobilized on a solid phase;

$c_1$) a labeled detection antibody directed against another of said epitopes, which are intact, of said protein of HCV;

$c_2$) and/or optionally a labeled detection antigen which comprises, or is, an antigenic fragment of a protein of HCV, said fragment comprising at least two destroyed epitopes, while at the same time conserving the ability to bind the anti-HCV antibodies possibly present in a biological sample.

Also preferentially, a kit according to the invention comprises a) the capture antigen which comprises, or is, an antigenic fragment of a protein of HIV, said fragment comprising at least one destroyed epitope, while at the same time conserving the ability to bind the anti-HIV antibodies possibly present in a biological sample;

b) a capture antibody directed against one of said epitopes, which are intact, of said protein of HIV;

said capture antigen and said capture antibody being immobilized on a solid phase;

c1) a labeled detection antibody directed against another of said epitopes, which are intact, of said protein of HIV; and/or c2) optionally a labeled detection antigen which comprises, or is, an antigenic fragment of a protein of HIV, said fragment comprising at least one destroyed epitope, while at the same time conserving the ability to bind the anti-HIV antibodies possibly present in a biological sample.

The kit may also comprise a means of detecting said antibodies present in the biological sample and forming complexes with said capture antigen, for example a labeled anti-immunoglobulin or anti-isotype antibody or else a detection antigen. The detection antigen is preferably an antigenic fragment, for example of a protein of HCV or of an HIV, which comprises at least one destroyed epitope, while at the same time conserving the ability to bind the antibodies (anti-HCV or anti-HIV) possibly present in the sample.

The kit may also comprise a detergent, more particularly a nonionic detergent, such as NP40 (Sigma) or any equivalent nonionic detergent known to those skilled in the art.

As described above, the capture antigen, like the detection antigen, may in particular be a fragment of the capsid protein of HCV, in which fragment at least one epitope site has been destroyed, and the capture and/or detection antibody is then selected so as to recognize said epitope site, which is intact, of the capsid protein.

In particular, a subject of the invention is a set of reagents comprising or consisting of a capsid peptide of HCV which is mutated at at least two distinct epitope sites, such as the peptide 1-75 (G34-G44-G47), and a pair of antibodies which cannot recognize the peptide 1-75 (G34-G44-G47) although they recognize the corresponding native HCV sequence.

When the microorganism detected is an HIV, the capture antigen, like the detection antigen, may in particular be a fragment of the gag protein of HIV, in which fragment at least one epitope site has been destroyed, and the capture and/or detection antibody is then selected so as to recognize said epitope site, which is intact, of the gag protein.

In particular, a subject of the invention is a set of reagents comprising or consisting of a peptide of the P25 protein which is mutated at at least one distinct epitope site, such as the peptide of sequence SEQ ID No. 22, and a pair of antibodies which cannot recognize the peptide of sequence SEQ ID No. 22 although they recognize the native sequence of the HIV-1 P25 protein.

The following figures and examples illustrate the invention without limiting the scope thereof.

LEGENDS OF THE FIGURES

FIG. 1 is a scheme illustrating a method of detection of the type such as those used prior to the invention, with, attached to a solid phase, a capture antibody and an unmodified capture antigen. This scheme illustrates the competition of the patient's antibody with the detection antibody, with respect to the binding to the capture antigen.

FIG. 2, by comparison, is a scheme illustrating an embodiment of the present invention. Since the capture antigen is mutated, it is no longer capable of being recognized by the detection antibody. There is therefore no longer any interference between the detection of the antibody and the detection of the antigen.

EXAMPLES

Detection of an Infection with the Hepatitis C Virus

Materials for Protocols 1a and 1b:

Anti-capsid monoclonal antibodies-peroxidase ("mAb-POD") conjugate: a conjugate of the anti-capsid monocloncal antibody, mAb 2 (see Table 1), labeled with peroxidase, is prepared according to the protocol described in patent application EP 0 752 102. This Peroxidase-labeled mAb2 antibody conjugate is diluted in the diluent of the 1st step (described below) so as to make it possible to ultimately obtain, with a well-documented positive sample, a high optical density (greater, for example, than 1.5 units), under conditions well known to those skilled in the art.

Another anti-capsid monoclonal antibody, mAb 1 (see Table 1), is also used, to be immobilized on the solid phase (see below).

Materials for Protocol 1c:

Anti-capsid monoclonal antibody-peroxidase ("mAb-POD") conjugate: a conjugate of the anti-capsid monoclonal antibody, mAb 1 (see Table 1), labeled with peroxidase, is prepared according to the protocol described in Patent application EP 0 752 102. This peroxidase-labeled mAb1 antibody conjugate is diluted in the diluent of the 1st step (described below) so as to make it possible to ultimately obtain, with a well-documented positive sample, a high optical density (greater, for example, than 1.5 units), under conditions well known to those skilled in the art.

Another anti-capsid monoclonal antibody, the anti-capsid monoclonal antibody mAb 3 (see Table 1), is also used, to be immobilized on the solid phase (see below).

Materials for Protocol 1d:
1) Anti-capsid monoclonal antibody biotin conjugate: a conjugate of the anti-capsid monoclonal antibody mAb 5 (see Table 1), labeled with biotin, is prepared according to the protocol described by Greg T. Hermanson in 1996. This biotin-labeled mAb 5 antibody is diluted in the diluent of the 1st step (described below) so as to make it possible to ultimately obtain, with a well-documented positive sample, a high optical density (greater, for example, than 1.5 units), under conditions well known to those skilled in the art.

Another anti-capside monoclonal antibody, the anti-capsid monoclonal antibody mAb 1 (see Table 1), is also used, to be immobilized on the solid phase (see below).

2) Peroxidase-labeled streptavidin conjugate: a conjugate of streptavidin labeled with peroxidase prepared according to the protocol described by Greg T. Hermanson in 1996. At the moment of use of protocol 1d, this peroxidase-labeled streptavidin conjugate is diluted in the diluent of the 2nd step (described below) so as to make it possible to ultimately obtain, with a well-documented positive sample, a high optical density (greater, for example, than 1.5 units), under conditions well known to those skilled in the art.

Common Materials for Protocols 1a, 1b, 1c and 1d:
1) Solid phase selected: Maxisorp microplate, Nunc (Denmark).
2) Diluents of the 1st and 2nd steps of the protocols according to the invention:

Diluent of the 1st step: Tris NaCl buffer, 0.05M, at pH 6.7, supplemented with 0.25% NP40 ((tert-octylphenoxy poly (oxyethylene) ethanol—IGEPAL CA 630, Sigma).

Diluent of the 2nd step: citrate buffer (50 mM, at pH 6.7, containing 20% glycerol, and containing a Peroxidase-labeled anti-human IgG (Fc) mouse polyclonal antibody conjugate (Jackson Immunoresearch Laboratories, USA) at a dilution making it possible to ultimately obtain, with a well-documented positive sample, a high optical density (greater, for example, than 1.5 units), under conditions well known to those skilled in the art.

3) Revealing solution: the revealing solution was composed
3a) of a substrate buffer: solution of citric acid (0.075M) and sodium acetate (0.1M), at pH 4.0, containing 0.015% $H_2O_2$ and 4% dimethyl sulfoxide (DMSO) (PROLABO), and
3b) of a chromogenic reagent: tetramethylbenzidine (TMB, Sigma) at a final concentration of 0.7 mM in the substrate buffer.
4) Stop solution: 1N $H_2SO_4$.

Methods:
Protocol 1a: Protocol for Simultaneously Detecting the Capsid Antigen of and the Antibodies Against (Anti-Capsid and Anti-NS3, NS4) the Hepatitis C Virus in a Sample (Serum or Plasma)

The principle of the assay is based on an immunoenzymatic method of the sandwich type for detecting the antigen, and of the indirect type for detecting the antibodies.

It is based on the following steps:
A coating solution is first of all prepared:
with a mixture of HCV antigens: a mutated peptide C-G-G-Cap 1-75 (G34-G44-G47) (capsid) comprising the sequence SEQ ID No. 4 and two recombined proteins produced by *Escherichia coli* from clones selected in the nonstructural regions NS3 (clone NS3.1: AA 1192-1492) and NS4 (clone 5-1-1: AA 1694-1735), and
with an anti-capsid monoclonal antibody (mAb 1), in 0.5M Tris buffer, pH 7.4.

The cupules of a microtitration plate (Nunc, Maxisorp) are then coated with the above solution in a proportion of 110 μl per cupule.

The microtitration plates are incubated overnight at ambient temperature (18-24° C.)

After removal of the coating solution, the plates are washed using a phosphate buffer (0.01M, pH 7.4) containing 0.1% of Tween 20, and then saturated by adding a phosphate buffer (0.01M, pH 7) containing 5% of sucrose, 25% of skimmed milk (Candiam™, France, or any other equivalent commercially available skimmed milk) and 10 mM of EDTA.

100 μl of 1st step diluent, containing the anti-capsid monoclonal antibody mAb 2 labeled with peroxidase, and then 50 μl of sample (serum or plasma) are successively distributed into each cupule.

The reaction medium is incubated at 37° C. for 1.5 hours. The HCV capsid antigens possibly present bind to the monoclonal antibody of the solid phase, mAb 1, and to the anti-capsid monoclonal antibody mAb 2 labeled with peroxidase, thus forming sandwich complexes with these two antibodies. Similarly, if anti-HCV antibodies are present, they bind to the antigens attached to the solid phase.

The plates are then washed (3 times) using a washing solution (Tris NaCl buffer, 0.01M, pH 7.4, supplemented with 0.1% Tween 20).

100 μl of $2^{nd}$ step diluent, containing the peroxidase-labeled anti-human IgG antibodies, are distributed into each cupule. The reaction medium is incubated at ambient temperature (18-24° C.) for 30 minutes. The labeled anti-human IgG antibodies in turn attach to the specific antibodies retained on the solid phase.

The plates are then washed (5 times) using a washing solution (Tris NaCl buffer, 0.01M, pH 7.4, supplemented with 0.1% Tween 20). The unbound anti-human IgG conjugate is thus eliminated.

100 μl of the revealing solution are added to each cupule. The reaction is allowed to develop in the dark for 30 minutes at ambient temperature (18-24° C.)

100 μl of stop solution are then distributed into each cupule.

After the reaction has been stopped, the optical density is read on a spectrophotometer at 450/620 nm.

Definition of the Threshold Value:
The threshold value was determined after statistical analysis of the specificity and sensitivity data using the ROC (Receiver Operating Characteristic) curve (Berck and Schultz, (1986)).

The specificity study related to 1000 samples from healthy individuals and the sensitivity study related to 200 HCV positive samples (in particular from the beginnings of seroconversion) from commercially available panels: BBI (Boston Biomedica Company, USA), Impath (USA), Serologicals (USA), Nabi (USA), ProMedDx (USA).

The threshold value is calculated, for each plate, from the signal obtained on a positive control, divided by a constant coefficient X specific for the test. It is approximately 0.280 OD (optical density) units in the examples presented.

As can be noted in this protocol, unlike some techniques of the prior art, the capture of the capsid antigen and that of the anti-capsid antibodies take place, in the present invention, on a single and same protein region of the capsid: the antigenic region capturing the anti-capsid antibodies (AA 1-75) clearly includes the region of antigenic specificity (AA 44-47) through which the immobilized anti-capsid antibody (mab 1) captures the capsid antigen. Thus, according to the invention, the loss of detection of a certain number of anti-capsid antibodies is reduced to a minimum and the sensitivity is improved accordingly.

Protocol 1b: Protocol for Simultaneously Detecting Capsid Antigen of and Antibodies Against (Anti-NS3 and NS4) the Hepatitis C Virus in a Sample (Serum or Plasma)

The principle of the assay is based on an immunoenzymatic method of the sandwich type to detect the antigen, and of the indirect type for detecting antibodies.

It is based on the following steps:

A coating solution is first of all prepared:
with a mixture of HCV antigens: two recombined Proteins produced by *Escherichia coli* from clones selected in the nonstructural regions NS3 (clone NS3.1: AA 1192-1492) and NS4 (clone 5-1-1: AA 1694-1735), and
with an anti-capsid monoclonal antibody (mAb 1), in 0.5M Tris buffer, pH 7.4.

The cupules of a microtitration plate (Nunc, Maxisorp) are then coated with the above solution in a proportion of 110 μl per cupule.

The subsequent steps are identical to those of protocol 1a.

Protocol 1c: Protocol for Simultaneously Detecting Capsid Antigen of and Antibodies Against (Anti-Capsid and Anti-NS3, NS4) the Hepatitis C Virus in a Sample (Serum or Plasma)

The principle of the assay is based on an immunoenzymatic method of the sandwich type for detecting antigen, and of the indirect type for detecting antibodies.

It is based on the following steps:

A coating solution is first of all prepared:
with a mixture of HCV antigens: a mutated peptide C-G-G-Cap 1-75 (G31-G44-G47) (capsid) comprising the sequence SEQ ID No. 5 or the mutated peptide C-G-G-Cap 1-53 (G31-G44-G47) comprising the sequence SEQ ID No. 11 or the mutated peptide C-G-G-Cap 6-68 (G31-G44-G47) comprising the sequence SEQ ID No. 8 and two recombined proteins produced by *Escherichia coli* from clones selected in the nonstructural regions NS3 (clone NS3.1: AA 1192-1492) and NS4 (clone 5-1-1: AA 1694-1735), and
with an anti-capsid monoclonal antibody (mAb 3), in 0.5M Tris buffer, pH 7.4.

The cupules of a microtitration plate (Nunc, Maxisorp) are then coated with the above solution in a proportion of 110 μl per cupule.

The microtitration plates are incubated overnight at ambient temperature (18-24° C.)

After removal of the coating solution, the plates are washed using a phosphate buffer (0.01M, pH 7.4) containing 0.1% of Tween 20, and then saturated by adding a phosphate buffer (0.01M, pH 7) containing 5% of sucrose, 25% of skimmed milk (Candia™, France, or any other equivalent commercially available skimmed milk) and 10 mM of EDTA.

100 μl of 1st step diluent, containing the anti-capsid monoclonal antibody mAb 1 labeled with peroxidase, and then 50 μl of sample (serum or plasma) are successively distributed into each cupule.

The reaction medium is incubated at 37° C. for 1.5 hours.

The HCV capsid antigens possibly present bind to the monoclonal antibody of the solid phase, mAb 3, and to the anti-capsid monoclonal antibody mAb 1 labeled with peroxidase, thus forming sandwich complexes with these two antibodies. Similarly, if anti-HCV antibodies are present, they bind to the antigens attached to the solid phase.

The subsequent steps are identical to those of protocol 1a.

As can be similarly noted here also, the capture of the capsid antigen and that of the anti-capsid antibodies take place, in the present invention, on a single and same protein region of the capsid: the antigenic region capturing the anti-capsid antibodies (AA 1-75) clearly includes the region of antigenic specificity (AA 29-34) through which the immobilized anti-capsid antibody (mab 3) captures the capsid antigen. Thus, according to the invention, the loss of detection of a certain number of anti-capsid antibodies is reduced to a minimum and the sensitivity is improved accordingly.

Protocol 1d: Protocol for Simultaneously Detecting Capsid Antigen of and Antibodies Against (Anti-Capsid and Anti-NS3, NS4) the Hepatitis C Virus in a Sample (Serum or Plasma)

The principle of the assay is based on an immunoenzymatic method of the sandwich type for detecting the antigen, and of the indirect type for detecting the antibodies.

It is based on the following steps:

A coating solution is first of all prepared:
with a mixture of HCV antigens: a mutated peptide C-G-G-Cap 1-75 (G34-G44-G47) (capsid) comprising the sequence SEQ ID No. 4, or a mutated peptide C-G-G-Cap 1-75 (G34-G46-G46') comprising the sequence SEQ ID No. 15 or a mutated peptide C-G-G-Cap 1-75 (G34-βA45) comprising the sequence SEQ ID No. 14 and two recombined proteins produced by *Escherichia coli* from clones selected in the nonstructural regions NS3 (clone NS3.1: AA 1192-1492) and NS4 (clone 5-1-1: AA 1694-1735), and
with an anti-capsid monoclonal antibody (mAb 1), 0.5M Tris buffer, pH 7.4.

The cupules of a microtitration plate (Nunc, Maxisorp) are then coated with the above solution in a proportion of 110 μl per cupule.

The microtitration plates are incubated overnight at ambient temperature (18-24° C.)

After removal of the coating solution, the plates are washed using a phosphate buffer (0.01M, pH 7.4) containing 0.1% of Tween 20, and then saturated by adding a phosphate buffer (0.01M, pH 7) containing 5% of sucrose; 25% of skimmed milk (Candia™, France, or any other equivalent commercially available skimmed milk) and 10 mM of EDTA.

100 μl of 1st step diluent, containing the anti-capsid monoclonal antibody mAb 5 labeled with biotin, and then 50 μl of sample (serum or plasma) are successively distributed into each cupule.

The reaction medium is incubated at 37° C. for 1.5 hours.

The HCV capsid antigens possibly present bind to the monoclonal antibody of the solid phase, mAb 1, and to the anti-capsid monoclonal antibody mAb 5 labeled with biotin, thus forming sandwich complexes with these two antibodies.

Similarly, if anti-HCV antibodies are present, they bind to the antigens attached to the solid phase.

The plates are then washed (3 times) using a washing solution (Tris, NaCl buffer, 0.01M, pH 7.4, supplemented with 0.1% Tween 20).

100 μl of 2nd step diluent, containing the peroxidase-labeled anti-human IgG antibodies and the peroxidase-labeled streptavidin, are distributed into each cupule.

The reaction medium is incubated at ambient temperature (18-24° C.) for 30 minutes. The labeled anti-human IgG antibodies in turn attach to the specific antibodies retained on the solid phase and the peroxidase-labeled streptavidin attaches to the biotinylated antibody mAb 5 retained on the same solid phase.

The subsequent steps are identical to those of protocol 1a.

As can be noted in the same way here also, the capture of the capsid antigen and that of the anti-capsid antibodies take place, in the present invention, on a single and same protein region of the capsid: the antigenic region capturing the anti-capsid antibodies (AA 1-75) clearly includes the region of antigenic specificity (AA 44-47) through which the immobilized anti-capsid antibody (mab 1) captures the capsid antigen. Thus, according to the invention, the loss of detection of a certain number of anti-capsid antibodies is reduced to a minimum and the sensitivity is improved accordingly.

Example 1

Detection of HCV Capsid Antigen in a Sample (Serum or Plasma), During the Serological Window Serum or plasma samples, taken from patients contaminated with HCV and grouped together in commercially available panels (Impath, USA), negative by antibody detection and positive by nucleic acid (PCR), were tested according to the method described in protocol 1a.

The results given in Table 2 are compared to results obtained by PCR.

TABLE 2

| Impath sample | Optical density | Interpretation | Antibody test | PCR test |
|---|---|---|---|---|
| 1866 | 0.616 | positive | negative | positive |
| 1883 (1/2)* | 0.661 | positive | negative | positive |
| 1889 (1/2)* | 0.671 | positive | negative | positive |
| 1999 (1/2)* | 0.596 | positive | negative | positive |
| 2028 (1/2)* | 0.520 | positive | negative | positive |
| 2144 (1/2)* | 0.674 | positive | negative | positive |
| 2145 (1/2)* | 0.808 | positive | negative | positive |
| 2159 | 0.547 | positive | negative | positive |
| 1959 | 0.512 | positive | negative | positive |

*dilution

It is noted that the results obtained using the method according to the invention correlate directly with the results obtained by PCR. The invention described therefore clearly makes it possible to detect the capsid antigens although the antibodies are not yet present, that is to say in samples taken within the serological window.

Example 2

Detection of Anti-Capsid Antibodies in Samples (Sera or Plasmas) Negative for HCV Antigen Serum or plasma samples, taken from patients contaminated with HCV and grouped together in internal and commercially available panels, positive for antibodies (capsid) and negative for antigen (capsid), were tested according to the methods described in protocols 1a and 1b.

In the absence of the peptide 1-75 (G34-G44-G47) (comprising SEQ ID No. 4) on the solid phase (protocol 1b), the samples tested (specific for the capsid) are not detected, whereas they are found to be positive with protocol 1a and in a conventional antibody test (cf. Table 3).

TABLE 3

| Sample | Optical density 1a | Optical density 1b | Interpretation 1a | Interpretation 1b | Antibody test |
|---|---|---|---|---|---|
| 16 | 0.942 | 0.092 | positive | negative | positive |
| 38 | 0.409 | 0.041 | positive | negative | positive |
| 49 | 3.246 | 0.080 | positive | negative | positive |
| KJ9-1102-0025 | 0.916 | 0.054 | positive | negative | positive |

The invention therefore makes it possible to detect, in patients contaminated with HCV, samples which are positive for anti-capsid antibodies and negative for capsid antigen.

Example 3

Simultaneous Detection of Capsid Antigen and of Anti-HCV Antibodies in a Sample (Serum or Plasma)

Two panels of samples of seroconversion PHV 907 and PHV 917 (i.e. two series of sera or plasmas, taken from two patients after infection with HCV or during seroconversion) marketed by BBI (Boston Biomedica Company, USA) were tested according to protocol 1a (cf. Tables 4 and 5).

TABLE 4

| Sample BBI | Day sample taken | Optical density | Interpretation | Antibody test | PCR test |
|---|---|---|---|---|---|
| 907-1 | 0 | 0.482 | positive | negative | positive |
| 907-2 | +4 | 0.344 | positive | negative | positive |
| 907-3 | +7 | 0.325 | positive | negative | positive |
| 907-4 | +13 | 0.318 | positive | negative | positive |
| 907-5 | +18 | 0.395 | positive | negative | positive |
| 907-6 | +21 | 0.855 | positive | positive | positive |
| 907-7 | +164 | 2.991 | positive | positive | positive |

TABLE 5

| Sample BBI | Day sample taken | Optical density | Interpretation | Antibody test | PCR test |
|---|---|---|---|---|---|
| 917-1 | 0 | 0.045 | negative | negative | negative |
| 917-2 | 13 | 0.803 | positive | negative | positive |
| 917-3 | 20 | 0.324 | positive | negative | positive |
| 917-4 | 22 | 0.448 | positive | negative | positive |
| 917-5 | 85 | 2.652 | positive | positive | negative |
| 917-6 | 131 | 2.582 | positive | positive | negative |
| 917-7 | 135 | 2.720 | positive | positive | positive |
| 917-8 | 138 | 2.736 | positive | positive | negative |
| 917-9 | 146 | 3.023 | positive | positive | negative |
| 917-10 | 152 | 3.033 | positive | positive | negative |

In Tables 4 and 5, a signal positive for antigen is observed, in a manner correlated to the presence of viral RNA (PCR test), with protocol 1a according to the invention; in the same way, a positive response is obtained on seroconversion samples, positive for antibodies and/or for antigen. This clearly shows that the 2 detections (capsid antigen and anti-capsid antibodies) can function simultaneously in the same assay and without interference.

In addition, the invention described is of value most particularly from a diagnostic point of view with respect to the PCR, since it makes it possible to detect samples which are negative by PCR and positive for antibodies.

Example 4

Comparison of the Performances of Various Mutated Peptides with Respect to the Detection of Anti-Capsid Antibodies Serum or plasma samples taken from patients contaminated with HCV, and grouped together in internal and commercially available panels, positive for antibodies (capsid) and negative for antigen (capsid), were tested according to the methods described in protocols 1c and 1d (cf. Tables 6 and 7).

TABLE 6 protocol 1c

| Sample | SEQ ID No. 5 | | SEQ ID No. 11 | | SEQ ID No. 8 | |
|---|---|---|---|---|---|---|
| | OD | Interp | OD | Interp | OD | Interp |
| 16 (1/2)* | 0.434 | pos | 0.534 | pos | 0.413 | pos |
| 21 (1/2)* | 0.520 | pos | 0.568 | pos | 0.481 | pos |
| 49 (1/20)* | 0.405 | pos | 0.538 | pos | 0.384 | pos |
| O7 | 0.312 | pos | 0.340 | pos | 0.285 | pos |

*dilution

TABLE 7 protocol 1d

| Sample | SEQ ID No. 4 | | SEQ ID No. 15 | | SEQ ID No. 14 | |
|---|---|---|---|---|---|---|
| | OD | Interp | OD | Interp | OD | Interp |
| 16 (1/2)* | 0.438 | pos | 0.362 | pos | 0.327 | pos |
| 21 (1/4)* | 0.257 | pos | 0.218 | neg | 0.197 | neg |
| 38 (1/2)* | 0.310 | pos | 0.221 | pos | 0.206 | neg |
| 49 (1/40)* | 0.308 | pos | 0.228 | pos | 0.201 | neg |
| BCP 453 (1/4)* | 0.363 | pos | 0.208 | neg | 0.175 | neg |
| KJ9-0025 (1/40)* | 0.263 | pos | 0.237 | pos | 0.212 | neg |

*dilution

The mutated peptides compared in Table 6 exhibit performances which are quite similar on the samples tested.

On the other hand, the differences in response between the peptides are more marked in Table 7. The peptides SEQ ID No. 15 and SEQ ID No. 14 do not make it possible to detect certain diluted anti-capsid samples, the same samples being recognized when tested pure.

Example 5

Influence of the Simultaneous Detection of Capsid Antigen and of Anti-HCV Antibodies on Diagnosis and the Decrease in the Serological Window Eight commercially available seroconversion panels (BEI, Boston Biomedica, US), (Impath, US) were tested with the protocol according to the invention (referred to as Combo assay) according to protocols 1a (with the peptide C-G-G-Cap 1-75 (G34-G44-G47) containing SEQ ID No. 4), 1c (with the peptide C-G-G-Cap 1-75 (G31-G44-G47) containing SEQ ID No. 5) and 1d (with the peptide C-G-G-Cap 1-75 (G34-G44-G47) containing SEQ ID No. 4).

Table 8 gives the results obtained by detection of antigen (Elisa assay) or of RNA (PCR), and by detection of antibodies and by Combo (formats 1a, 1c and 1d) on these various seroconversions. For 4 seroconversions out of 8, protocols 1a, 1c and 1d make it possible to detect the first positive sample concomitantly with the appearance of the viral RNA detected by PCR. The average number of days between the detection of antigen and the detection of antibodies corresponding to the reduction in the serological window is 33 days for the two protocols 1a, 1c and 1d.

TABLE 8

| IMPATH/ BBI panel | Delay (days) relative to the 1st day of HCV RNA detection | | | | | Reduction in the serological window with the Combo test Days |
|---|---|---|---|---|---|---|
| | HCV Ag | HCV Ab | Combo HCV 1a | Combo HCV 1c | Combo HCV 1d | |
| 6211 (NS3) | 0 | 46 | 10 | 10 | NT | 36 |
| 6225 (NS3) | 0 | 33 | 2 | 2 | 2 | 31 |
| 6227 (CAP-NS3-NS4) | 0 | 32 | 4 | 4 | 4 | 28 |
| 6229 (NS3) | 0 | 24 | 0 | 0 | 0 | 24 |
| 9041 (NS3) | 0 | 38 | 3 | 3 | 3 | 35 |
| 907 (CAP) | 0 | 13 | 0 | 0 | 0 | 13 |
| 6222 (CAP-NS3) | 0 | 23 | 0 | 0 | 0 | 23 |
| 917 (CAP-NS3) | 0 | 72 | 0 | 0 | 0 | 72 | mean = 33 days

NT = not tested

Example 6

Comparison of Performances and Classification of Various Techniques on Seroconversion Sera 21 commercially available seroconversion panels (BBI, Boston Biomedica Company, USA; Impath, USA), exhibiting different specificities, were tested with the test according to the invention according to protocols 1a and 1c, and with a series of commercially available tests, which are in fact among the best according to the classification produced by the MDA (Medical Devices Agency) in the United States in February 2002. This comparison takes into account the number of days of delay in detection relative to the detection of RNA (PCR test). Thus, the kit exhibiting the smallest general mean is the most effective in terms of earliness of detection (Table 9).

TABLE 9

| Impath/BBI panel | Results expressed in days of delay in detection relative to PCR | | | | | | | Target antigen |
|---|---|---|---|---|---|---|---|---|
| | Invention protocol 1a | Invention protocol 1c | Invention protocol 1d | Vitros Eci anti-HCV | Axsym HCV version3 | "Ortho HCV 3.0 short incubation" | Access HCV Ab Plus | |
| 907 | 0 | 0 | 0 | 13 | 18 | 18 | 13 | CAP |
| 909 | 0 | 0 | 0 | 28 | 33 | 28 | 28 | CAP |
| 912 | 4 | 4 | 4 | 7 | 7 | 7 | 7 | CAP |
| 913 | 0 | 0 | 0 | 2 | 12 | 7 | 7 | CAP |
| 914 | 0 | 0 | 0 | 16 | 16 | 16 | 16 | CAP |
| 6215 | 0 | 0 | 0 | 20 | 20 | 20 | 20 | CAP |
| Subtotal | 4 | 4 | 4 | 86 | 106 | 96 | 91 | |
| 904 | 9 | 9 | 9 | 9 | 9 | 9 | 18 | NS3 |
| 915 | 12 | 12 | 12 | 12 | 5 | 14 | 17 | NS3 |
| 6212 | 23 | 23 | 23 | 12 | 12 | 12 | 23 | NS3 |
| 6224 | 19 | 19 | 19 | 19 | 19 | 19 | 19 | NS3 |
| 9041 | 3 | 3 | 3 | 62 | 62 | 62 | 62 | NS3 |
| 9044 | 0 | 0 | 0 | 25 | 21 | 25 | 25 | NS3 |
| 9047 | 0 | 0 | 0 | 28 | 28 | 28 | 28 | NS3 |
| Subtotal | 66 | 66 | 66 | 167 | 156 | 169 | 192 | |
| 905 | 11 | 11 | 11 | 14 | 14 | 14 | 21 | NS3/CAP |
| 908 | 19 | 19 | 19 | 13 | 11 | 19 | 19 | NS3/NS4 |
| 910 | 5 | 5 | 0 | 8 | 8 | 8 | 8 | CAP/NS4 |
| 911 | 0 | 0 | 0 | 14 | 14 | 14 | 14 | CAP/NS3-NS4 |
| 917 | 0 | 0 | 0 | 72 | 72 | 72 | 72 | NS3/CAP |
| 6213 | 32 | 26 | 26 | 26 | 26 | 32 | 32 | CAP/NS3-NS4 |
| 6214 | 30 | 30 | 30 | 30 | 25 | 30 | 30 | NS3/NS4 |
| 6222 | 0 | 0 | 0 | 21 | 21 | 21 | 21 | CAP/NS3 |
| Subtotal | 97 | 91 | 86 | 198 | 191 | 210 | 217 | |
| General mean | 7.9 | 7.7 | 7.4 | 21.5 | 21.6 | 22.6 | 23.8 | |

▒ Last sample not detected: = 3d added arbitrarily

The results generated with protocols 1a, 1c and 1d according to the invention allow an earlier detection of HCV infection (only 8 days of delay on average relative to the PCR for protocol 1a, 7.7 days for protocol 1c and 7.4 days of delay for protocol 1d), before the appearance of the antibodies.

Thus, the test described according to the invention takes first place in this classification, this being with the three protocols (1a, 1c and 1d) which make use of pairs of antibodies and mutated peptides which are different.

In conclusion, the results obtained with protocols 1a, 1c and 1d according to the invention clearly show that the latter effectively makes it possible to detect infection with HCV very early, with a sensitivity quite close to that of PCR, while at the same time making it possible to follow the patient's serological evolution after seroconversion

Example 7

Study of Specificity on the Three Combo Protocols 1a, 1c and 1d

The study of specificity was carried out on sera from blood donors (originating from the Etablissement Français du Sang, Rungis, France). The results obtained for the various protocols 1a, 1c and 1d have been given, respectively, in Tables 10, 11 and 12.

TABLE 10

Protocol 1a

| | |
|---|---|
| Number of sera found to be negative | 968 |
| Confirmed reactive sera | 1 |

TABLE 10-continued

| Protocol 1a | |
|---|---|
| Confirmed reactive sera (%) | 99.9 |
| Mean of negatives for ratio (OD sample/threshold value) | 0.23 |
| Standard deviation | 0.77 |
| Number of standard deviations for the threshold value | 10 |

TABLE 11

| Protocol 1c | |
|---|---|
| Number of sera found to be negative | 2475 |
| Confirmed reactive sera | 6 |
| Confirmed reactive sera (%) | 99.8 |
| Mean of negatives for ratio (OD sample/threshold value) | 0.14 |
| Standard deviation | 0.063 |
| Number of standard deviations for the threshold value | 13.9 |

TABLE 12

| Protocol 1d | |
|---|---|
| Number of sera found to be negative | 2475 |
| Confirmed reactive sera | 4 |
| Confirmed reactive sera (%) | 99.8 |
| Mean of negatives for ratio (OD sample/threshold value) | 0.18 |
| Standard deviation | 0.055 |
| Number of standard deviations for the threshold value | 14.8 |

Good performances in terms of specificity are noted, whatever the protocol (1a, 1c or 1d) used.

As may have been noted throughout this description, the HCV Combo test according to the invention is, surprisingly, capable, by virtue of the capture of the capsid antigen and that of the anti-capsid antibodies on a single and same protein region of the capsid, of providing a sensitivity close to that of the PCR and better than that of certain techniques of the prior art.

This result is surprising since, in modifying the target capsid peptides, the inventors were taking the risk of losing the detection of a certain significant number of antibodies.

Example 8

Detection of an Infection with the Human Immunodeficiency Virus (HIV-1)

The method described in the present invention also applies to the detection of infection due to any type of infectious microorganism (for instance viruses, such as, for example, the viruses responsible for the various types of hepatitis, retroviruses, in particular the retroviruses responsible for AIDS in humans (HIV-1, HIV-1 group 0, HIV-2) or monkeys, the cytomegalovirus (CMV), flaviviruses, including the dengue viruses, and also bacteria, microbial parasites, etc.) for which simultaneous detection of antigens and antibodies is desirable.

Example 8 shows the application of the present invention to the simultaneous detection of the P25 (gag) viral antigen of the human immunodeficiency virus (HIV-1) and of anti-P25 antibodies.

Common Materials for Protocols a, b and c:
1) Solid phase selected: Maxisorp microplate, Nunc (Denmark).
2) Diluent of the 1st step: Tris, NaCl buffer, 0.05M, at pH 6.7, supplemented with 0.25% NP40 (IGEPAL CA 630, Sigma).
3) Diluent of the 2nd step: Tris, NaCl buffer, 0.01M, PH 7.4, supplemented with 0.1% Tween 20.
4) Revealing solution: the revealing solution was composed
4a) of a substrate buffer: solution of citric acid (0.075M) and of sodium acetate (0.1M), at pH 4.0, containing 0.015% $H_2O_2$ and 4% dimethyl sulfoxide (DMSO) (PROLABO), and
4b) of a chromogenic reagent: tetramethylbenzidine (TMB, Sigma) at a final concentration of 0.7 mM in the substrate buffer.
5) Stop solution: 1N $H_2SO_4$.

Materials of Protocol a: Detection of Anti-HIV1 P25 Antibodies

Mutated synthetic peptide corresponding to the following sequence

SEQ ID No. 22

$_{293}$FRGYVGRFYKTLRAEQAGQGVKNFMTETLLVQNANPDCKTILKAL GPAATLEEMMTAC$_{350}$ and comprising the mutations (G295-G298-G310-G312-F316) compared to the consensus sequence of the P25 protein of HIV-1 M, namely SEQ ID No. 23

$_{293}$FRDYVDRFYKTLRAEQASQEVKNWMTETLLVQNANPDCKTILKAL GPAATLEEMMTAC$_{350}$

Peroxidase-labeled anti-human IgG (H+L) sheep polyclonal antibody conjugate (Bio-Rad). This conjugate is diluted, before use, in the diluent of the 2nd step (described above) so as to make it possible to ultimately obtain, with a well-documented positive sample, a high optical density, under conditions well known to those skilled in the art.

Materials for Protocol b: Detection of HIV-1 P25 Antigen

Anti-P25 monclonal antibody Pm25 which recognizes the following sequence of the HIV-1 M P25 protein (SEQ ID No. 24)

$_{308}$QASQEVKNWMTETLL$_{322}$

Conjugate of monoclonal antibody Pm25 described above labeled with peroxidase. This conjugate is diluted, before use, in the diluent of the 2nd step (described above) so as to make it possible to ultimately obtain, with a well-documented positive sample, a high optical density, under conditions well known to those skilled in the art.

Materials for Protocol c: Simultaneous ("Combo") Detection of Anti-P25 Antibodies and of HIV-1 P25 Antigen Mutated synthetic peptide corresponding to the following sequence SEQ ID No. 22

$_{293}$FRGYVGRFYKTLRAEQAGQGVKNFMTETLLVQNANPDCKTILKAL GPAATLEEMMTAC$_{350}$

Monoclonal antibody Pm25 which recognizes the following sequence of the HIV-1 M P25 protein $_{308}$QASQEVKNWMTETLL$_{322}$ (SEQ ID No. 24)

Peroxidase-labeled anti-human IgG (H+L) sheep polyclonal antibody conjugate (Bio-Rad).

Conjugate of monoclonal antibody Pm25 described above labeled with peroxidase.

The 2 immunoperoxidase conjugates above are diluted together, before use, in the diluent of the 2nd step (described above) so as to make it possible to ultimately obtain, with a well-documented positive sample, a high optical density, under conditions well known to those skilled in the art.

Methods:

Protocol a: Detection of Anti-HIV-1 P25 Antibodies

The principle of the assay is based on an immunoenzymatic method of the indirect type for detecting the anti-HIV-1 P25 antibodies.

It is based on the following steps:

A coating solution is first of all prepared with the mutated peptide SEQ ID No. 22 (G295-G298-G310-G312-F316) comprising the sequence SEQ ID No. 22 in carbonate buffer, pH 9.6.

The cupules of a microtitration plate (Nunc, Maxisorp) are then coated with the solution above in a proportion of 110 µl per cupule.

The microtitration plates are incubated overnight at ambient temperature (18-24° C.)

After removal of the coating solution, the plates are washed using a phosphate buffer (0.01M, pH 7.4) containing 0.1% of Tween 20, and then saturated by adding a phosphate buffer (0.01M, pH 7) containing 5% sucrose and 25% skimmed milk (Candia™, France, or any other equivalent commercially available skimmed milk).

80 µl of 1st step diluent and then 20 µl of sample (serum or plasma) are successively distributed into each cupule.

The reaction medium is incubated at 37° C. for 1 hour. If anti-HIV-1 P25 antibodies are present, they bind to the Peptide attached to the solid phase.

The plates are then washed (3 times) using a washing solution (Tris, NaCl buffer, 0.01M, pH 7.4, supplemented with 0.1% Tween 20).

100 µl of 2nd step diluent, containing the peroxidase-labeled anti-human IgG (H+L) antibodies, are distributed into each cupule. The reaction medium is incubated at ambient temperature (18-24° C.) for 30 minutes. The labeled anti-human IgG (H+L) antibodies in turn attach to the specific antibodies retained on the solid phase.

The plates are then washed (5 times) using a washing solution (Tris, NaCl buffer, 0.01M, pH 7.4, supplemented with 0.1% Tween 20). The unbound anti-human IgG conjugate is thus eliminated.

100 µl of the revealing solution are distributed into each cupule. The reaction is allowed to develop in the dark for 30 minutes at ambient temperature (18-24° C.)

100 µl of stop solution are then distributed into each cupule.

After the reaction has been stopped, the optical density is read on a spectrophotometer at 450/620 nm.

Protocol b: Detection of the HIV-1 P25 Antigen

The principle of the assay is based on an immunoenzymatic method of the sandwich type for detecting HIV-1 P25 antigen. It is based on the following steps:

A coating solution is first of all prepared with the anti-HIV-1 P25 monoclonal antibody (Pm25) in carbonate buffer, pH 9.6.

The cupules of a microtitration plate (Nunc, Maxisorp) are then coated with the above solution in a proportion of 110 µl per cupule.

The subsequent steps are identical to those for protocol a, up to the second step.

For the second step, 100 µl of 2nd step diluent, containing the peroxidase-labeled monoclonal antibody Pm25, are distributed. The reaction medium is incubated at ambient temperature (18-24° C.) for 30 minutes. The labeled monoclonal antibody Pm25 then attaches to the P25 antigen retained on the solid phase, when it is present.

The final steps are identical to those of protocol a.

Protocol c: Simultaneous ("Combo") Detection of the HIV-1 P25 Antigen and of Anti-HIV-1 P25 Antibodies in a Sample (Serum or Plasma)

The principle of the assay is based on an immunoenzymatic method of the sandwich type for detecting antigen, and of the indirect type for detecting antibodies.

It is based on the following steps:

A coating solution is first of all prepared:
with the mutated peptide SEQ ID No. 22 (G295-G298-G310-G312-F316), and
with the anti-P25 monoclonal antibody (Pm25) in carbonate buffer, pH 9.6.

The cupules of a microtitration plate (Nunc, Maxisorp) are then coated with the above solution in a proportion of 110 µl per cupule.

The microtitration plates are incubated overnight at ambient temperature (18-24° C.)

After removal of the coating solution, the plates are washed using a phosphate buffer (0.01M, pH 7.4) containing 0.1% of Tween 20, and then saturated by adding a phosphate buffer (0.01M, pH 7) containing 5% of sucrose and 25% of skimmed milk (Candia™, France, or any other equivalent commercially available skimmed milk).

80 µl of 1st step diluent and then 20 µl of sample (serum or plasma) are successively distributed into each cupule.

The reaction medium is incubated at 37° C. for 1 hour. The P25 antigen possibly present binds to the monoclonal antibody of the solid phase. Similarly, if anti-P25 antibodies are present, they bind to the antigenic peptide attached to the solid phase.

The subsequent steps are identical to those of protocol 1a, up to the second step.

For the second step, 100 µl of 2nd step diluent, containing the peroxidase-labeled monoclonal antibody Pm25 and the peroxidase-labeled anti-human IgG (H+L) antibodies, are distributed. The reaction medium is incubated at ambient temperature (18-24° C.) for 30 minutes. The labeled monoclonal antibody Pm25 then attaches to the P25 antigen retained on the solid phase. Similarly, the labeled anti-human IgG (H+L) antibodies in turn attach to the specific antibodies retained on the solid phase.

The final steps are identical to those of protocol a.

Results:

| Sample | Protocol a (O.D.) | Protocol b (O.D.) | Protocol c (O.D.) |
| --- | --- | --- | --- |
| Positive for anti-P25 antibodies | | | |
| Sample 1 | 0.138 | — | 0.316 |
| Sample 2 | 0.513 | — | 0.946 |
| Positive for P25 antigen | | | |
| No. 1 | — | 1.104 | 1.151 |
| No. 2 | — | 0.587 | 0.695 |
| Negative for anti-P25 antibodies and for P25 antigen | | | |
| Sample 3 | 0.045 | 0.051 | 0.125 |
| Sample 4 | 0.025 | 0.049 | 0.179 |

As may be noted in the same way here also, the capture of the HIV-1 P25 antigen and that of the anti-HIV-1 P25 antibodies take place, in the present invention, on a single and same protein region of the capsid the antigenic region capturing the anti-P25 antibodies (AA293-350) clearly includes the region of antigenic specificity (AA308-322) through which the immobilized anti-P25 antibody (Pm25) captures the P25 antigen.

It goes without saying that those skilled in the art, using the present Example 8, for example, as a basis, may also easily carry out an immunoassay for simultaneously detecting the HIV-1 P25 (gag) antigen, anti-HIV-1 P25 antibodies and antibodies directed against the gp41 glycoprotein (envelope) of HIV-1. For detecting the anti-HIV-1 gp41 antibodies, use may, by way of nonexhaustive example, be made of either whole, natural or recombined gp41, which is in itself known, or a peptide containing the immunodominant epitope of gp41, such as that described by the publication J W. Gnann et al. (1987).

Immunoassays for simultaneously detecting the HIV-2 P26 (gag) antigen, anti-HIV-2 P26 antibodies and antibodies directed against the gp36 glycoprotein (envelope) of HIV-2 are also part of the invention. Those skilled in the art may, for detecting the P26 antigen, make use of anti-P26 antibodies, which are known in themselves, and for detecting the anti-P26 antibodies, make use of antigenic peptides of P26, for example, which can be derived from the HIV-2 sequence published by Guyader et al. (1987). For detecting the anti-gp36 antibodies, those skilled in the art may, by way of nonexhaustive example, make use either of whole, natural or recombined gp36, which is known in itself, or a peptide containing the immunodominant epitope of gp36, such as that described by the publication J W. Gnann et al. (1987).

They will also be able to easily carry out a "HIV-1+ HIV-2 Combo" immunoassay simultaneously combining detection of the HIV-1 P25 antigen, of the HIV-2 P26 antigen, of the anti-HIV-1 P25 antibodies, of the anti-HIV-2 P26 antibodies, of the anti-HIV-1 gp41 antibodies and of the anti-HIV-2 gp36 antibodies, which is also part of the invention.

BIBLIOGRAPHICAL REFERENCES

Alcon et al., J. of Clin. Microbiol., 2002, vol. 40(2), pp. 376-381
Atherton at al. (1989) "solid phase peptide synthesis, a practical approach", IRL Press, Oxford University Press, pp. 25-34
Benoit et al, (1982) PNAS USA, 79, pp. 917-921
Berck et Schultz, (1986), Arch. Pathol. Lab. Ivied., 10, pp. 13-20
Bukh, Semin. Liver Dis. (1995) 15: 41-63
Cerino at al., (1991), J. Immunology, Vol. 147(8), pp. 2692-2696
Clayes et al. (1995), J of Medical Virology, 45, pp. 273-281
Garson at al., (1990) Lancet, 336, pp. 878-879
Gnann, J W., et al. (1987) Science, 237: pp. 1346-1349
Guyader et al. (1987) Nature 326, pp. 662-669
Hajime Tokita et al. (2000) J. Olin. Microbial, Vol. 38, pp. 3450-3452
Harlow et al. (1988) ed., "Antibodies: a laboratory manual"
Hermanson Greg T., (1996) Bioconjugate techniques, Academic Press, New York, pp. 373-380 at pp. 580-583
Hosein et al. (1991) PNAS Vol. 88, May, pp. 3647-3651
Icardi et al. (2001) J. Clin. Microbiol., 39, pp. 3110-3114
Ishida, (1993), J. Olin. Microbial., Vol. 31, No. 4, pp. 936-940
Köhler et Milstein, (1975) Nature, 256, pp. 495-497
Leahy et al. (1991) Third International Symposium on HCV, Strasbourg, poster B35
Maiolini et al., (1978) Journal of Immunological Methods, 20, pp. 25-34
Marks at al. (1991) J. Mol. Biol, 222, pp. 581-597
Merrifield (1963) J. Amer. Chem. Soc, 85, pp. 2149-2154
Nasoff et al. (1991) PNAS Vol. 88, No. 12, pp. 5462-5466
Okamoto et al. (1990a) Japan J. Exp. Med., vol. 60(3), pp. 167-177
Okamoto et al. (1990b) Japan J. Exp. Med., vol. 60(4), pp. 223-233
Peterson et al. (2000) Vox sanguinis, Vol. 78, pp. 80-85
Ratner et al. (1985) Nature, 313, pp. 277-284
Sällberg et al. (1992) J. Clin. Microbiology, Vol. 30(8), pp. 1989-1994
Sanchez-Pescador et al. (1985) Science, 227, pp. 484-492
Scott et al. (1990), Science, 249, pp. 386-390
Sheppard, in <<Peptides 1971>>, Nesvadba H (ed.) North Holland, Amsterdam, p. 111
Shieh et al. (1991) Laboratory Investigation Vol. 65, No. 4, pp. 408-411
Simmonds, (1995), Hepatology, 21, pp. 570-583
Stuyver et al. (1994), P.N.A.S. USA, 91, pp. 10134-10138
Takahashi et al. (1992) J. Gen. Virol., Vol. 73(3), London, pp. 667-672
Wain-Hobson et al. (1985) Cell, 40, pp. 9-17
Yang et al. (1995) Clin. Exp Immunol., 101, pp. 272-277
Yang et al. (1999), J of Medical Virology, 57, pp. 345-350

The invention claimed is:

1. A kit which is of use for detecting an infection with human immunodeficiency virus (HIV) in a biological sample, comprising:
   a) a capture or detection antigen which comprises an antigenic fragment of a gag protein of HIV, said fragment comprising at least one destroyed epitope, while at the same time conserving the ability to bind the antibodies directed against HIV possibly present in the biological sample; and
   b) a capture or detection antibody directed against said epitope, which is intact, of said gag protein of HIV;
   wherein the antigenic fragment comprises sequence FRGYVGRFYKTLRAEQAGQGVKN-FMTETLLVQNANPDCKTILKALGPAATL-EEMMTAC SEQ ID NO: 22.

2. The kit as claimed in claim 1, in which the antibody is an antibody for capturing the HIV antigen present in the biological sample.

3. The kit as claimed in claim 1, in which the antibody recognizes an epitope of sequence QASQEVKNWMTETLL (SEQ ID NO: 24).

4. The kit as claimed in claim 1 further comprising, besides the capture antigen, means of detecting the anti-HIV antibodies present in the biological sample, the detecting means forming complexes with the capture antigen.

5. The kit as claimed in claim 4, wherein the detecting means is a labeled anti-immunoglobulin or anti-isotype antibody.

6. The kit as claimed in claim 1, wherein the capture antibody and the capture antigen are present in a form immobilized on a solid phase.

7. The kit as claimed in claim 6, further comprising:
   c1) a labeled detection antibody directed against another of the epitopes, which are intact, of the HIV protein; and
   c2) optionally a labeled detection antigen which is an antigenic fragment of the gag protein of HIV, the fragment comprising at least one other destroyed epitope, while at the same time conserving the ability to bind the anti-HIV antibodies possibly present in a biological sample.

8. The kit as claimed in claim 1, also comprising at least one detergent of the nonionic type.

9. The kit as claimed in claim 8, wherein the at least one detergent is NP40.

* * * * *